United States Patent
Alberts et al.

(10) Patent No.: US 11,471,111 B2
(45) Date of Patent: Oct. 18, 2022

(54) PERFORMANCE TEST FOR EVALUATION OF NEUROLOGICAL FUNCTION

(71) Applicant: THE CLEVELAND CLINIC FOUNDATION, Cleveland, OH (US)

(72) Inventors: Jay L. Alberts, Chagrin Falls, OH (US); Richard A. Rudick, Solon, OH (US); David D. Schindler, Chagrin Falls, OH (US); Joshua Hirsch, Brecksville, OH (US); Stephen M. Rao, Chagrin Falls, OH (US); Francois Bethoux, Shaker Heights, OH (US); Susan Linder, Olmsted Falls, OH (US); Deborah Miller, Cleveland Heights, OH (US)

(73) Assignee: THE CLEVELAND CLINIC FOUNDATION, Cleveland, OH (US)

(*) Notice: Subject to any disclaimer, the term of this patent is extended or adjusted under 35 U.S.C. 154(b) by 528 days.

(21) Appl. No.: 16/666,864

(22) Filed: Oct. 29, 2019

(65) Prior Publication Data
US 2020/0155020 A1 May 21, 2020

Related U.S. Application Data

(63) Continuation of application No. 14/102,230, filed on Dec. 10, 2013, now Pat. No. 10,470,679.
(Continued)

(51) Int. Cl.
*A61B 5/11* (2006.01)
*A61B 5/16* (2006.01)
(Continued)

(52) U.S. Cl.
CPC .......... *A61B 5/7275* (2013.01); *A61B 5/1101* (2013.01); *A61B 5/112* (2013.01);
(Continued)

(58) Field of Classification Search
CPC ......... A61B 5/24; A61B 5/1101; A61B 5/112; A61B 5/1121; A61B 5/1124; A61B 5/162;
(Continued)

(56) References Cited

U.S. PATENT DOCUMENTS 6,066,105 A 5/2000 Guillen
7,640,804 B2 1/2010 Daumer et al.
(Continued)

FOREIGN PATENT DOCUMENTS

WO WO-8707969 A * 12/1987 ........... G06F 19/324
WO 2012/063982 A1 5/2012

OTHER PUBLICATIONS

Spain, R. I., et al. "Body-worn motion sensors detect balance and gait deficits in people with multiple sclerosis who have normal walking speed." Gait & posture 35.4 (2012): 573-578.
(Continued)

*Primary Examiner* — David J. McCrosky
(74) *Attorney, Agent, or Firm* — Tarolli, Sundheim, Covell & Tummino LLP

(57) ABSTRACT

This disclosure relates to a system and method to implement a performance test to help evaluate a patient's neurological and cognitive function. The performance test can be executed by the patient autonomously using a portable computing device, such as a tablet computer or smart phone. The portable computing device can be programmed to execute a set of modules configured to assess motor and cognitive performance, such as a manual function test module, a cognitive processing speed test module, and a movement assessment test module. The set of modules can also include a collection module to aggregate test data from the manual function test module, the cognitive processing speed test module, and the movement assessment test module.

20 Claims, 18 Drawing Sheets

Related U.S. Application Data

(60) Provisional application No. 61/885,193, filed on Oct. 1, 2013, provisional application No. 61/885,223, filed on Oct. 1, 2013, provisional application No. 61/735,321, filed on Dec. 10, 2012.

(51) Int. Cl.
    *A61B 5/00*     (2006.01)
    *A61B 5/24*     (2021.01)

(52) U.S. Cl.
    CPC .......... *A61B 5/1121* (2013.01); *A61B 5/1124* (2013.01); *A61B 5/162* (2013.01); *A61B 5/24* (2021.01); *A61B 5/4023* (2013.01); *A61B 5/4082* (2013.01); *A61B 5/743* (2013.01)

(58) Field of Classification Search
    CPC ... A61B 5/4023; A61B 5/4082; A61B 5/7275; A61B 5/743
    See application file for complete search history.

(56) References Cited

U.S. PATENT DOCUMENTS

| | | |
|---|---|---|
| 8,868,369 B2 | 10/2014 | Esser et al. |
| 9,320,330 B2 | 4/2016 | Cooke et al. |
| 9,451,916 B2 | 9/2016 | Curtiss |
| 2006/0251307 A1 | 11/2006 | Florin et al. |
| 2013/0281888 A1 | 10/2013 | Bender et al. |
| 2014/0092055 A1 | 4/2014 | Radivojevic et al. |
| 2014/0330159 A1 | 11/2014 | Costa et al. |

OTHER PUBLICATIONS

Phi, Alexis. "What is the Gyroscope Inside the iPad and What's in It for You." Stuff Review (2011): Mar. 2011.

Fischer, J. S., et al. "The Multiple Sclerosis Functional Composite measure (MSFC): an integrated approach to MS clinical outcome assessment." Multiple Sclerosis Journal 5.4 (1999): 244-250.

Polman, Chris H., and Richard A. Rudick. "The multiple sclerosis functional composite: a clinically meaningful measure of disability." Neurology 74.17 Supplement 3 (2010): S8-S15.

Rosenblum, Sara, and Patrice L. Tamar Weiss. "Evaluating functional decline in patients with Multiple Sclerosis." Research in developmental disabilities 31.2 (2010): 577-586.

PCT International Search Report and Written Opinion for corresponding International Application Serial No. PCT/US2013/074164, dated Mar. 17, 2014, pp. 1-10.

\* cited by examiner

PERFORMANCE TEST FOR EVALUATION OF NEUROLOGICAL FUNCTION

RELATED APPLICATIONS

This application is a continuation of U.S. patent application Ser. No. 14/102,230, filed Dec. 10, 2013 and claims the benefit of U.S. Provisional Patent Application Ser. No. 61/735,321, filed Dec. 10, 2012, entitled "MULTIPLE SCLEROSIS PERFORMANCE TEST." This application also claims the benefit of U.S. Provisional Patent Application Ser. No. 61/885,223, filed Oct. 1, 2013, entitled "MULTIPLE SCLEROSIS PERFORMANCE TEST." This application also claims the benefit of U.S. Provisional Patent Application Ser. No. 61/885,193, filed on 1 Oct. 2013, and entitled OBJECT RECOGNITION BY TOUCH SCREEN, the entire contents of which is incorporated herein by reference. Each of the above-identified applications is hereby incorporated by reference in its entirety.

TECHNICAL FIELD

This disclosure relates generally to a performance test for evaluation of neurological function, and more specifically to a system and method that can implement the performance test to evaluate a patient's neurological and/or cognitive function.

BACKGROUND

Various diseases and disorders can adversely affect an individual's neurological and/or cognitive function. For example, multiple sclerosis (MS) is a chronic, progressive disease of the central nervous system (CNS), in which the myelin sheaths of axons of the brain, spinal cord and optic nerve become damaged, resulting in an inflammatory response. MS can lead to demyelination and scarring, as well as a broad spectrum of signs and symptoms, which often progresses to physical and cognitive disability.

MS-related disability ranges from minimal to severe, and evolution of disease manifestations over time is variable—both in the specific nature of the symptoms and disability and in the rate of deterioration. The historical approach to measuring MS-related disability has been use of a neurologist rating scale, called the Kurtzke Expanded Disability Scale (EDSS). The EDSS rates disease severity using a 20 point scale, ranging from 0 to 10 in 0.5 point increments, with increasing numbers reflecting increased disability. However, the EDSS has been criticized because it is neither precise nor quantitative. A newer approach has been to evaluate MS disease severity using a 3-part composite, called the Multiple Sclerosis Functional Composite (MSFC). The MSFC is a three-part, standardized, quantitative, assessment instrument for use in clinical studies, particularly clinical trials of MS. The MSFC can produce scores for each of the three individual measures—walking, arm function, and cognitive function—as well as a composite score. However, since the MSFC measures are administered in person by a trained examiner, its usefulness outside of clinical settings tends to be impaired.

SUMMARY

In an example, a non-transitory computer-readable medium is described that stores instructions executable by one or more processors to perform a method. The manual dexterity of a given patient can be evaluated in response to a first set of user inputs during execution of a manual dexterity test module and corresponding manual dexterity test data indicative of the given patient's manual dexterity can be provided for further processing. The cognitive function of the given patient can be evaluated in response to a second set of user inputs during execution of a cognitive processing speed test module and corresponding cognitive function test data indicative of the given patient's cognitive function can be provided for further processing. The center-of-gravity movement of the given patient can be evaluated in response to motion data acquired during execution of at least one motion test module and corresponding motion test data indicative of the given patient's center-of-gravity movement over a test duration can be provided for further processing. The manual dexterity test data, the cognitive function test data, and the motion test data can be aggregated to provide an aggregate set of test data for the given patient.

In another example, a mobile computing device is described that includes memory to store computer executable instructions corresponding to an application and data and a processor configured to access the memory and execute the computer executable instructions corresponding to the application. The application includes a manual function test module to evaluate the manual dexterity of a given patient in response to a first set of user inputs based on a manual dexterity test executed by the manual function test module and to store corresponding manual dexterity test data in the memory based on the first set of user inputs indicative of a measure of the given patient's manual dexterity; a cognitive processing speed test module to evaluate the cognitive function of the given patient in response to a second set of user inputs based on a cognitive processing speed test and to store corresponding cognitive function test data in the memory based on the second set of user inputs indicative of the given patient's cognitive function; a movement assessment test module to evaluate center-of-gravity movement of the given patient in response to motion test data acquired during a physical activity of the given patient and store the motion test data in the memory indicative of the center-of-gravity movement of the given patient; and a collection module to aggregate test data based on the manual dexterity test data, the cognitive function test data and the motion test data.

In another example, a computer-implemented method is described for testing cognitive and motor abilities of a given patient. The manual dexterity of the given patient can be evaluated in response to a first set of user inputs during execution of a manual dexterity test module and corresponding manual dexterity test data indicative of the given patient's manual dexterity can be provided for further processing. The cognitive function of the given patient can be evaluated in response to a second set of user inputs during execution of a cognitive processing speed test module and corresponding cognitive function test data indicative of the given patient's cognitive function can be provided for further processing. The center-of-gravity movement of the given patient can be evaluated in response to motion data acquired during execution of at least one motion assessment module and corresponding movement test data indicative of the given patient's center-of-gravity movement over a test duration can be provided for further processing. The manual dexterity test data, the cognitive function test data, and the movement test data can be collected. Each of the manual dexterity test module, the cognitive processing speed test module, and the at least one motion assessment module can be executed on a mobile computing apparatus in response to user inputs by the given patient.

DETAILED DESCRIPTION

This disclosure provides systems and methods that can be utilized to implement a performance test to assess a patient's neurological and cognitive function. The patient can have a neurological condition that affects cognitive and motor performance, such as multiple sclerosis (MS) or other neurological disorders (e.g., Parkinson's, essential tremor, stroke, concussion, etc.). For example, the performance test can be used to determine the severity of the neurological condition in the patient. Although the systems and methods are described herein with respect to MS and the MS performance test (MSPT), it will be understood that patients with a neurological disorder other than MS can also benefit from the cognitive-motor performance assessment described herein.

The approach assessing cognitive-motor performance according to the systems and methods described herein can be easily implemented outside of clinical settings by patients themselves or family members. For example, the systems and methods can be executed using a portable computing device, such as a tablet computer or smart phone, which is configured with one or more accelerometers and a gyroscope. The portable computing device can be programmed to execute a set of modules configured to assess cognitive-motor performance, such as a manual function test module, a cognitive processing speed test module, and a movement assessment test module (and other test modules that can be used to assess the cognitive-motor performance). The set of modules can also include a collection module to aggregate test data from the manual function test module, the cognitive processing speed test module, and the movement assessment test module (as well as other test modules that can be used to assess the cognitive-motor performance. The tests can be implemented to measure neurological function and/or neuropsychological function of a subject. For example, the tests can be employed as a test for MS severity as part of a clinical trial or other research protocol, or for patient monitoring for clinical assessment and care.

The tests can be self-administered by the subject, as opposed to by a trained technician; however, a trained technician can also administer such tests, if desired. This is enabled because the application of each test module and associated score scoring is automated by executable instructions programmed to process acquired testing data and to score tests based on testing data acquired during each of the tests by the computer via which the tests are administered. In some examples, the data from these tests can be aggregated at the computing device and transmitted to a provider database via a network. This process or sending the test data can also be automated. The test data can be collected (e.g., in a database) for many patients for a variety of evaluative purposes, such as to facilitate patient monitoring and drug development.

Figure 1:
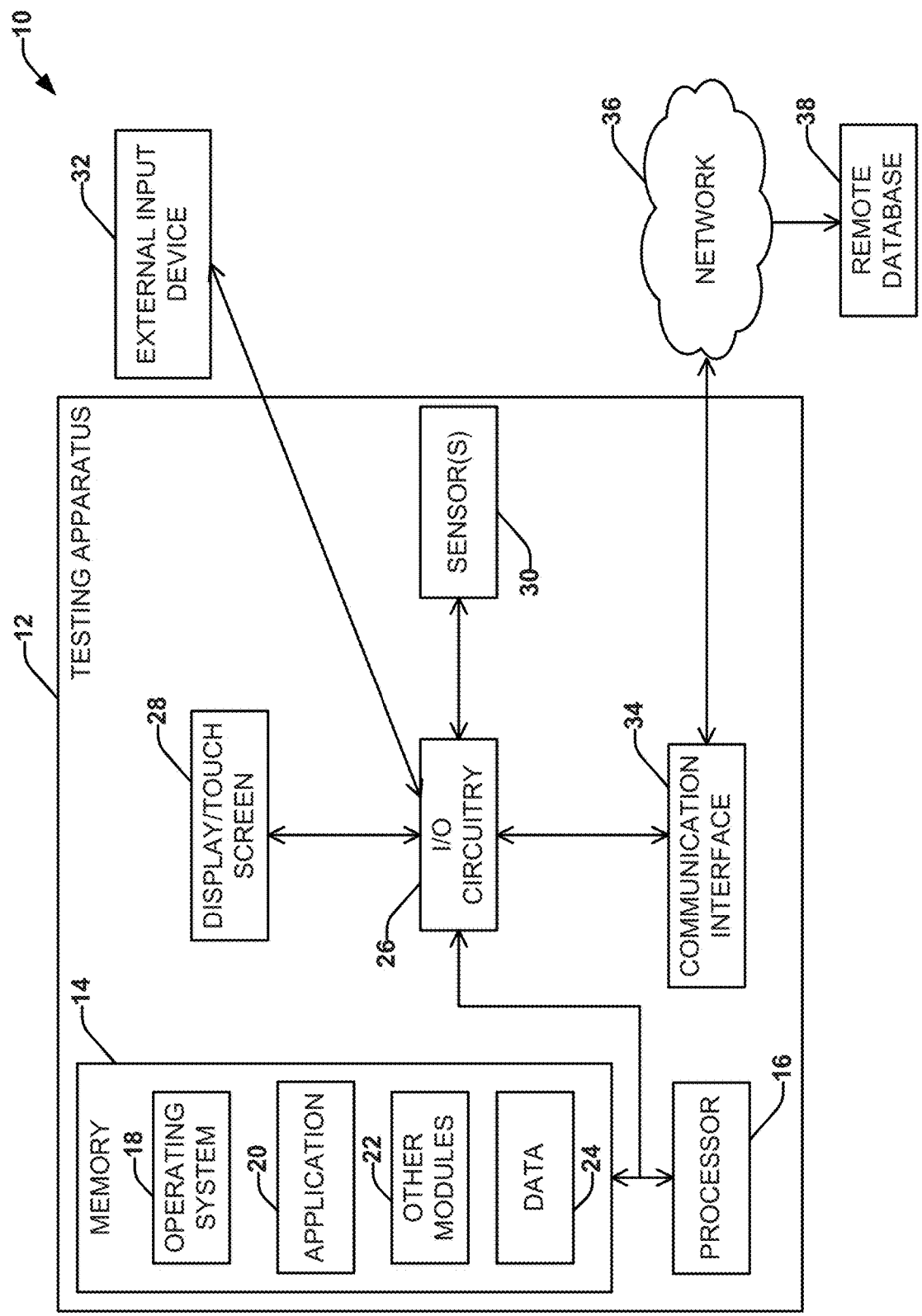
FIG. 1 depicts an example of a system that can implement a performance test to produce results that can be used to evaluate a patient's neurological and cognitive function.

FIG. 1 depicts an example of a system 10 that can be employed for testing and analysis of one or more patients. The system 10 can include one or more computing apparatuses (also referred to as testing apparatuses) 12 programmed to execute a plurality of tasks based on instructions stored in memory 14. The computing apparatus 12 can be implemented as a portable computer, such as a tablet computer or smart phone. As such, the device includes a display/touch screen 28 that provides a human-machine interface (HMI) that a user, such as a patient, can employ to interact with the computing apparatus 12. As used herein a patient can refer to a living subject (e.g., adult or child) in need of treatment by a physician, physician assistant, advanced practice registered nurse, veterinarian, or other health care provider or the subject may be a healthy subject that is to be tested for other reasons.

In some examples, a user can perform a series of tasks that involve physical interaction between the patient (e.g., using one or more fingers) and the touch screen 28 directly to manipulate one or more graphical objects displayed on the screen. In other examples, user can perform certain tasks through interaction with an external input device 32 that can be communicatively coupled with the system 10 (e.g., via physical or wireless connection with a corresponding port of the apparatus 12). The interaction may involve contact between the external input device 32 and the display 28 or otherwise be responsive to the instructions and/or graphical elements presented on the display. In still other examples, the apparatus 12 can include one or more sensors 30 (e.g., one or more accelerometers, a gyrometer or gyroscope) that can collect data in two or three dimensions responsive to patient movement and interactions during selected tasks.

As an example, the sensor 30 can include one or more three-axis accelerometers. The one or more accelerometers can be configured to measure acceleration of the apparatus along one or more axis, such as to provide an indication of acceleration (e.g., an acceleration vector) of the apparatus in three dimensions. The one or more accelerometers can measure the static acceleration of gravity in tilt-sensing applications, as well as dynamic acceleration resulting from motion or shock. Additionally, the one or more accelerometers can possess a high resolution (4 mg/LSB) that can enables measurement of inclination changes less than 1.0°, for example. The one or more accelerometers may provide various sensing functions, such as activity and inactivity sensing to detect the presence or lack of motion and if the acceleration on any axis exceeds a user-defined level. The one or more accelerometers can also sense tapping (e.g., single and double taps) on a surface such as a touch screen as well as sense free-fall if the device is falling. These and other sensing functions can provide output data. An example accelerometer is the ADXL345 digital accelerometer available from Analog devices. Of course other accelerometers could be utilized.

As another example, the sensor 30 can include a three-axis gyroscope (e.g., gyrometer) that can be configured to sense orientation of the device along three orthogonal axes. The gyroscope can provide output data corresponding to orientation of the apparatus 12 along three orthogonal axes. The gyroscope can be implemented as 3-axis MEMS gyro IC, such as including three 16-bit analog-to-digital converters (ADCs) for digitizing the gyro outputs, a user-selectable internal low-pass filter bandwidth, and a Fast-Mode I²C (400 kHz) interface. The gyroscope 30 can also include an embedded temperature sensor and a 2% accurate internal oscillator. An example gyroscope that can be utilized is the ITG-3200 3 IC available from InvenSense, Inc. Other gyroscopes could be utilized in other examples.

In the example of FIG. 1, the system 10 can include input/output (I/O) circuitry 26 configured to communicate data with various input and output devices coupled to the system 10. In the example of FIG. 1, the I/O circuitry 26 is connected to communicate with the display/touch screen 28, the sensor 30, the external input device 32 and a communication interface 34. For example, the communication interface 34 can include a network interface that is configured to provide for communication with corresponding network 36, such as can include a local area network or a wide access network (WAN) (e.g., the internet or a private WAN) or a combination thereof.

As a further example, the communication interface 34 can send task data and/or analysis data derived from task data to a remote database 38. For instance, the system 10 can be programmed upload and transfer such data to the remote database 38, such as an electronic health record (EHR) for the patient. Such transfer of data can be HIPPA compliant and provided over a secure tunnel (e.g., HTTPS or the like). The transfer of task data and/or analysis data can be automated to occur upon completion of one or more tests. The data provided by the apparatus 12 can further be analyzed by an external analysis system. The analysis system can access the database directly (e.g., within a firewall where the database 38 resides or it may access the database via the network 36 via a secure link. A provider may also employ an EHR system or other interface to access the test results stored in the database 38. In this way, statistical analysis of a large patient population can be performed based on data collected from a plurality of different apparatuses, which can be distributed across a state, region, country or even the world. Moreover, since the set of tasks can be performed by patients using a portable computing apparatus (e.g., tablet computer) 12 in the absence of a trained healthcare professional, a single provider or team of providers can monitor and service needs of a much larger patient population than would otherwise be possible for traditional MS testing, which typically requires that each patient visit and travel to a testing site for evaluation. Additionally, the approach disclosed herein can provide a patient-centric neurological and neuropsychological performance self-assessment system. By implementing such testing in the system as part of a self-administered testing platform, related scoring and analysis can be generated by the computer automatically because data is collected by such computer, obviating the need for human involvement, and allowing error-free score generation. As mentioned above, the analysis and scoring can relate to evaluation of a patient's neurological function and/or neuropsychological function for the patient.

The computing apparatus 12 can also include a processing unit (also referred to as processor) 16 and memory 14. The memory 14 can include one or more non-transitory memory device configured to store machine readable instructions and/or data. The memory 14 could be implemented, for example as volatile memory (e.g., RAM), nonvolatile memory (e.g., a hard disk, flash memory, a solid state drive or the like) or combination of both. The processing unit 16 (e.g., a processor core) can be configured in the system for accessing the memory 14 and executing the machine-readable instructions. A user may enter commands and information into the computing apparatus 12 through one or more external input devices, such as the touch screen 28 or other user input devices (e.g., a force transducer and stylus apparatus, microphone, a joystick, a game pad, a scanner, or the like) 32. Such external devices could be coupled to the computing system via the I/O circuitry 26.

By way of example, the memory 14 can store a variety of machine readable instructions and data, including an operating system 18, one or more application programs 20, other program modules 22, and program data 24. The operating system 18 can be any suitable operating system or combinations of operating systems, which can depend on manufacturer and system to system. In some examples, the application programs and program modules for implementing the functions of the test apparatus disclosed herein can be downloaded and stored in the memory 14 for execution by the processor 16. The application programs 20, other program modules 22, and program data 24 can cooperate to provide motor and cognitive testing via the computing apparatus 12, such as disclosed herein. Additionally, application programs 20, other program modules 22, and program data 24 can be used for computing an indication of motor, cognitive or a combination of motor and cognitive functions of a patient based on the task data acquired during testing, such as disclosed herein.

As a further example, the application programs 20 can be programmed to implement a battery of tests designed to gather task data for evaluation of a patient's MS condition. For example, the system 10 can include the following test modules programmed to collect data 24, including a manual function test module, a cognitive processing speed test module, and a movement assessment test module (and other test modules that can be used to assess the cognitive-motor performance). The movement assessment test module can include one or both of a balance test module and a gait assessment module. The data 24 can be analyzed to characterize the patient's cognitive and motor performance, individually or both simultaneously, to provide a quantitative assessment of the patient's MS condition. The data 24 can be analyzed separately for each of a plurality of individual tests to compute a score for each test. Additionally or alternatively, the data 24 for the set of tests can be aggregated to compute an overall score for the patient, which can also be stored in the memory 14 as part of the data 24. The analysis of the data 24 can be performed at the apparatus 12, which is programmed to execute such testing. In other examples, the analysis of the data 24 can be performed remotely, such as by the remote system in response to the data being uploaded from the apparatus 12 to the remote database 38.

Regardless of whether the analysis is performed by the apparatus 12 or by a remote analysis system, since the analysis of the data can be performed by a computer according to test data, the analysis can provide a more robust characterization of the neurological, neuropsychological and cognitive functioning. As a result, the approach disclosed herein can in turn ascertain more useful information in distinguishing MS or other conditions from excepted norms, and further distinguish severity within a condition and over time for each patient, such as based on a historical analysis of test data over period of time (e.g., one or more years). Additionally, such data can be automatically entered into clinical or research databases, thereby eliminating the need for manual entry of data by a human, and allowing error-free data entry.

Figure 2:
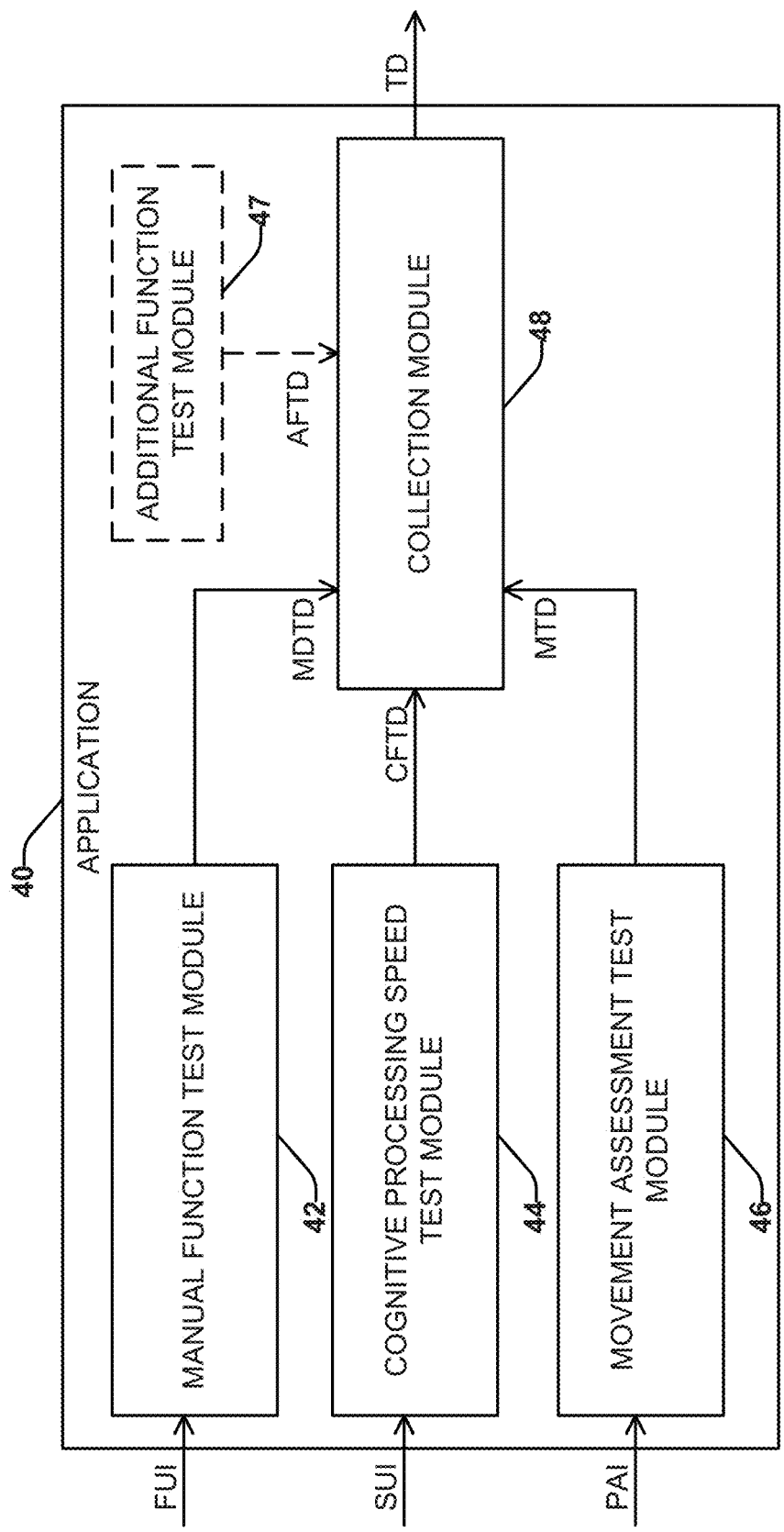
FIGS. 2 and 3 depict examples of applications that can be used to produce the results that can be used to evaluate a patient's neurological and cognitive function.
Figure 3:
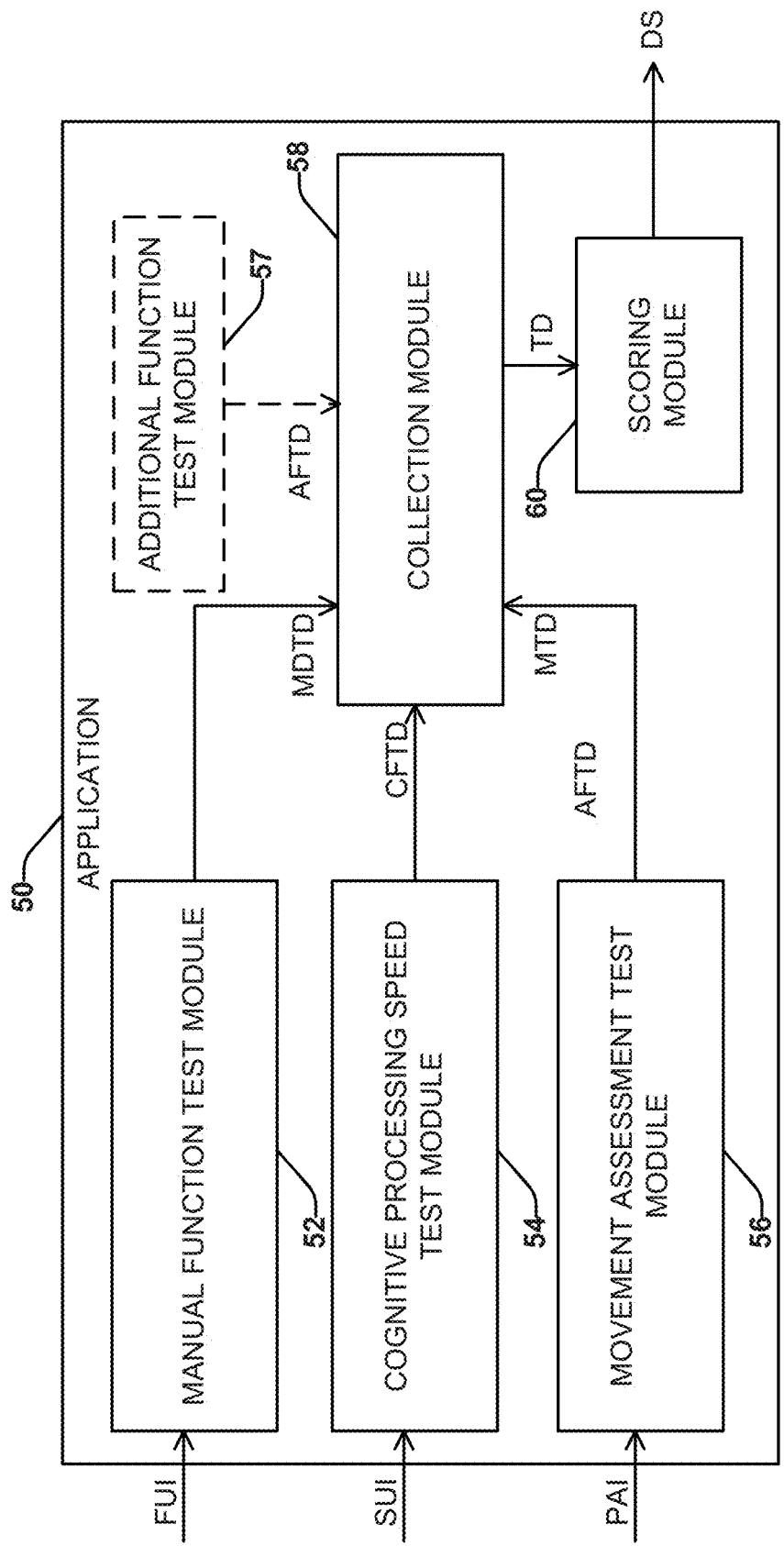

FIGS. 2 and 3 depict examples of respective applications (e.g., implemented as machine readable instructions) 40, 50 that can be used to produce the results test data that can be used to evaluate a patient's neurological and cognitive function. Each of the applications 40, 50 can be stored in the memory 14 of FIG. 1 and be executed by the processor 16 of FIG. 1, for example. The applications 40, 50 each include machine readable instructions for an MS performance test (MSPT) and corresponding data that can be programmed to test and evaluate MS status and/or condition of a patient. The applications 40, 50 each include modules that can employ a plurality of discreet tasks that capture corresponding data.

In the examples of FIGS. 2 and 3, the modules include a manual function test module 42, 52; a cognitive processing speed test module 44, 54; a movement assessment test module 46, 56; and a collection module 48, 58. The applications 40, 50 can also include one or more additional function test modules 47, 57. Application 50 also includes a scoring module 60. The manual function test module 42, 52 can evaluate a manual dexterity of a given patient in response to a first set of user inputs (FUI) based on a manual dexterity test executed by the manual function test module 42, 52. The manual function test module 42, 52 can store corresponding manual dexterity test data (MDTD) in the memory based on the first set of user inputs (FUI) indicative of a measure of the given patient's manual dexterity. The cognitive processing speed test module 44, 54 can evaluate a cognitive function of the given patient in response to a second set of user inputs (SUI) based on a cognitive processing speed test. The cognitive processing speed test module can store corresponding cognitive function test data (CFTD) in the memory based on the second set of user inputs (SUI) indicative of the given patient's cognitive function. The movement assessment test module 46, 56 can evaluate center-of-gravity movement of the given patient in response to motion test data (MTD) acquired during a physical activity (PAI) of the given patient. The movement assessment test module 46, 56 can store the motion test data (MTD) in the memory indicative of the center-of-gravity movement of the given patient. The collection module 48, 58 can aggregate test data (TD) based on the manual dexterity test data (MDTD), the cognitive function test data (CFTD) and the motion test data (MTD). The collection module 48, 58 can also aggregate data (AFTD) from any additional function test module 47, 57 into the test data (TD).

The modules of applications 40, 50 can execute tests (also referred to as tasks or trials) that provide outputs that can be utilized to characterize the cognitive and motor state of the patient. The tasks can be programmed to provide and/or coordinate with a graphical user interface (GUI) that displays graphics corresponding to the test. The modules and/or tests can be programmed to collect data in response to user inputs and user interactions during the test. The data acquired during testing can vary based on the test being performed, the test module being executed, and the input devices activated to provide input data. The arrangement of this data and specificity can depend on application requirements and user preferences. Each of the applications 40, 50 can sample active input devices for each test module and test combination, along which related data (e.g., identifying timing, test ID, module ID) to facilitate analysis thereof. The sample rate for a given input source further can vary depending on the input device operating parameters and the information being collected.

Examples of input data that can be collected can include accelerometer data, gyroscope data, GUI data, UI device data and analysis data. The accelerometer data that can be acquired by sampling an output of one or more accelerometers (e.g., sensors 30 of FIG. 1) to provide an indication of acceleration along one or more orthogonal axes. The gyroscope data can be acquired by sampling an output of a gyroscope (also referred to as a gyrometer). The GUI data can represent user interactions received in response to user input (e.g., as can be made via display/touch screen 28 of FIG. 1) during a respective test. Text and graphical objects can be visualized on a touch screen to instruct the user for performing the various tests for each respective test module. The GUI data can also include graphical and other information that is provided as part of the test and results of the test responsive to user interactions. For example, the results and other information in the GUI data can include timing information obtained during the test, based on a system clock (e.g., of the computing apparatus 12 of FIG. 1) to provide timing information for when user inputs are received. Analysis and meaning attributed to the GUI data depending on the context of the test and test module being executed can also be stored, such as forming part of the GUI data or the analysis data.

The data can also include user input (Up/device data that includes data collected from one or more user input device (e.g., from external device 32 of FIG. 1) during a respective test. For example, the user input device can include a single axis or multi-axis force (torque) transducer that can be utilized to measure a gripping force and associated coordination of a given patient under test. The device can be in the form of a cone-shaped or cylindrical structure to be gripped by the user and includes force transducer to measure the user's gripping force. In some examples, the gripping structure can be utilized to engage graphical objects presented on a display (e.g., a touch screen) via user interactions. The interactions can be detected via the touch screen to provide corresponding GUI data. Thus, it is understood, that the input data recorded for a given test can involve more than one type of data from one or more different input sources. In some example, the input device can also include other sensors (e.g., accelerometers and a gyroscope) such as to provide additional information associated with movement of the gripping structure by the user during the test. Depending on the capabilities of the UI/device data and test requirements, the UI/device data can also include other information relevant to tests or the test environment, such as timing information (e.g., timestamp applied to other data), temperature, altitude, user inputs received via user inputs at the device and the like. Thus, the input data can include a combination of data from disparate and separate devices (e.g., from a gripping device and from the touch screen) that can be utilized to perform each respective test. The type of movement and interactions requested can vary from test to test.

In the example of FIG. 2, the analysis of the test data (TD) can be performed by a remote analysis system, while in the example of FIG. 3, the analysis of the test data (TD) can be performed by a scoring module 60 and a disability score (DS) can be provided to the remote database. The scoring module 60 can, for example, characterize the cognitive and motor abilities of the given patient based on percentiles of neurological normal function for the manual dexterity test data, the cognitive function test data and the motion test data. It will be appreciated that the scoring function and/or scoring module 60 can use another means to determine the cognitive and motor abilities of the patient with respect to neurological normative values that gives an understanding of the patient's disease state and/or progression.

The scoring module 60 can compute one or more score that can be used to evaluate the cognitive and motor abilities of the patient. The score can be a score for a given test, such as implemented by each of the test modules 52-58. In other examples, the score can be a combined score based on result data collected based on tasks executed for two or more of the test modules. In yet other examples, individual tasks of a given test can also be analyzed to compute a respective score. Each of the scores, regardless of the manner computed, can be stored in memory as part of the analysis data. As mentioned, the scoring function can be programmed to compute each score automatically based on the test data acquired by each respective test module.

Additionally, since each of the tests can be implemented according to respective test modules, each respective module can be updated independently as new data and testing paradigms might become available. Thus the MSPT application is scalable and extensible.

Figure 4:
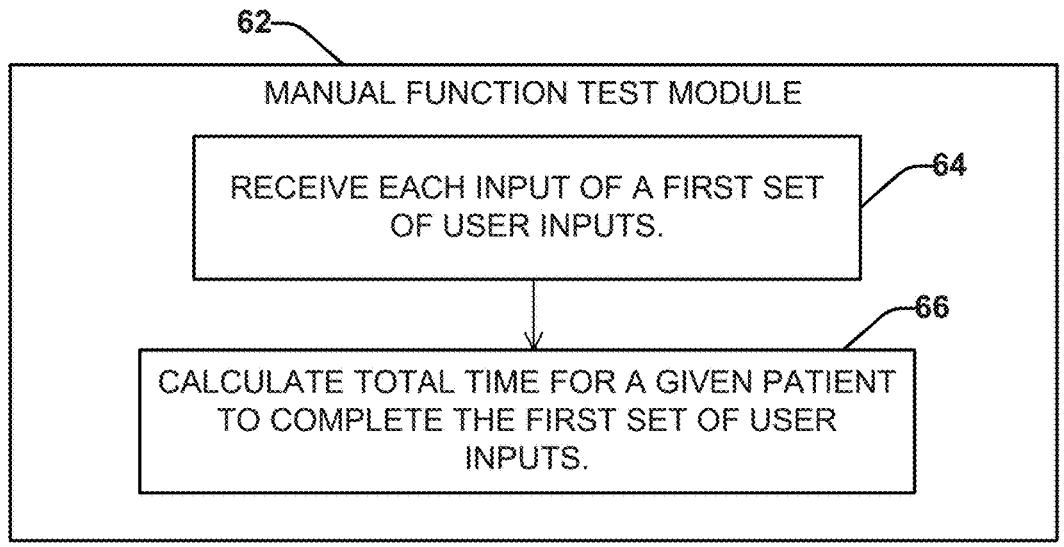
FIG. 4 depicts an example of a manual performance test module that can be used to evaluate a patient's manual dexterity.
Figure 5:
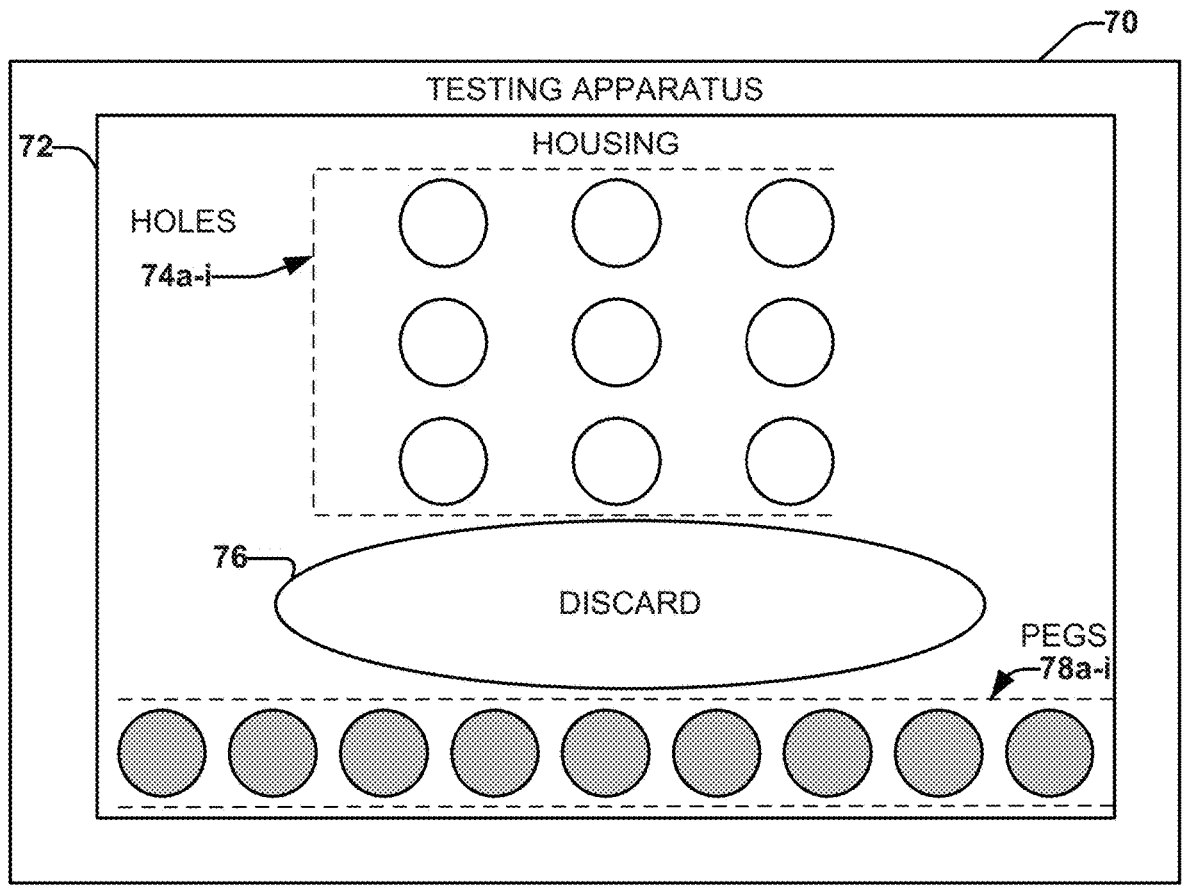
FIG. 5 depicts a schematic example of an upper extremity test that can be used to evaluate a patient's manual dexterity.
Figure 6:
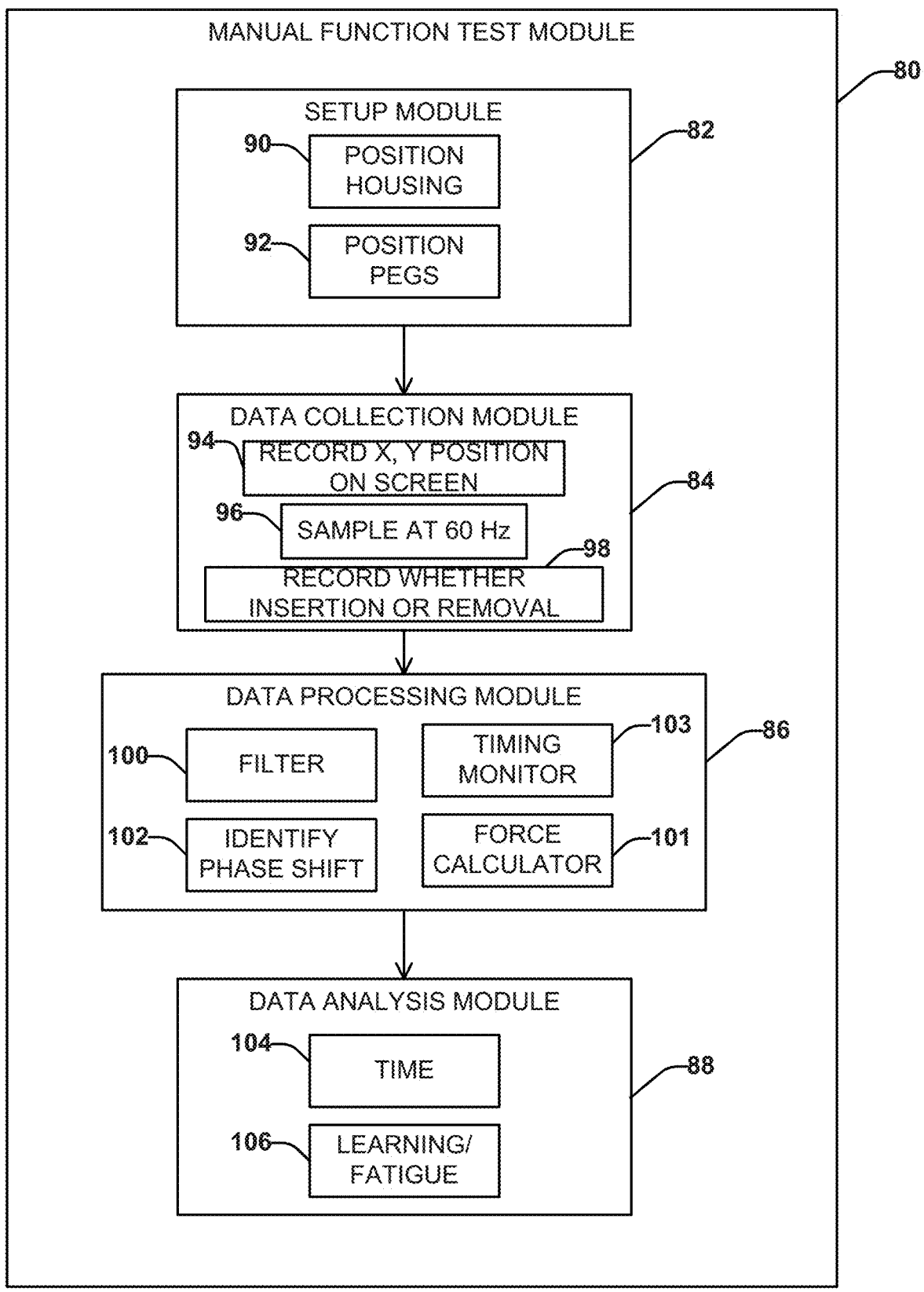
FIG. 6 depicts an example flow diagram demonstrating execution of a manual function test module.

Examples of the manual performance test module that can be used to evaluate a patient's manual dexterity are shown in FIGS. 4-6. FIG. 4 depicts an example of a manual performance test module 62 that can be used to evaluate a patient's manual dexterity. FIG. 5 depicts a schematic example 70 of a nine-hole peg test that can be used in conjunction with a touch screen computing device to evaluate the patient's manual dexterity. FIG. 6 depicts an example flow of the execution of the manual function test module 80.

FIG. 4 depicts an example of a manual performance test module 62 that can be used to evaluate the patient's manual dexterity. The user actions can be prompted by graphical and/or audible indicators to initiate the test. At element 64, the first set of user inputs can be received, each in sequence, by the computing device (e.g., a tablet computer or a smart phone). The user inputs can be, for example, a touch by a user's finger or a peg device to a touch screen or the mobile computing device. At element 66, the total time for the given patient to complete the first set of user inputs can be calculated. Other parameters can also be calculated (e.g., force, time for individual tasks, and the like). The total time (and other parameters) can be an output and/or a result of the manual function test module that is part of the test data and scored by a scoring function.

FIG. 5 depicts a schematic illustration of an example implementation of a testing apparatus 70 corresponding to a computer-implemented (e.g., electronic) analog of a nine-hole peg test that can be used to evaluate the patient's manual dexterity. A housing 72 can be placed on a touch-sensitive screen of the testing apparatus (e.g., a tablet computer) 70, which can exposing a GUI and provide access to the touch screen through apertures (or holes) 74a-i. Pegs 78a-i can be inserted into the apertures 74a-i, and the touch screen can detect when the pegs are in contact with the GUI.

An example of the housing 72 and pegs 78 that can be utilized in conjunction with a apparatus 70 having a capacitive touch screen is disclosed in the above-incorporated U.S. provisional patent application No. 61/885,193, which is incorporated herein by reference. For example, when an object (e.g., one of the pegs 78) engages the surface of the touch screen (e.g., a capacitive touch screen) with or without human contact, an electrically conductive path can be established extending from the touch-sensitive surface. The path can establish a sufficient flow of electrons to enable the electrical characteristics (e.g., capacitance) of the touch-screen to change so that the engagement can be detected even in the absence of human contact. Since the peg can be detected by the touch-sensitive surface in the absence of contact by the subject, based on an electrically conductive path that is established when a given peg is inserted into a hole to contact the touch-sensitive surface, each peg can be detected during the test even after it is released by the user.

The manual dexterity test module can track data related to the nine-hole peg test, including, but not limited to: a position of at least one peg, as well as various times, including the time to complete the nine-hole peg test, a time for peg insertion, a time for peg removal, and/or a force used to insert or remove the peg. In one example of the test, the test is initiated with the pegs inserted in a row at the bottom of the screen, as demonstrated in FIG. 5. Thus, each peg is detected by the touch screen in the row, resulting in a graphical indicator being displayed on the screen at the location corresponding to each peg. The test ends when all of the pegs are returned to their starting positions in the row. The timing for moving each peg from the row to one of the nine holes can be computed automatically by the computing device and utilized for assessing the dexterity of the user.

In a second example of the test, designed to more closely simulate the traditional 9-hole peg test, the pegs are placed in the center bowl (such as indicated in FIG. 5 by "DISCARD" at 76. The test ends after the pegs have been inserted into and removed from all the wholes and all pegs are returned to the discard bowl. Various instructions can be visible through the housing and/or adjacent to the housing (in an uncovered portion of the screen) to help guide the user through one or more tests.

FIG. 6 shows example flow of the execution of the manual function test module 80 that can quantify manual dexterity during the performance of an upper extremity task. The manual function test module 80 can include a plurality of sub-modules, each of which can include respective functions. As shown in FIG. 6, the sub-modules can include a setup module 82, a data collection module 84, a data processing module 86 and a data analysis module 88. FIG. 6 is described with respect to a tablet computer and the electronic analog of the nine-hole peg test of FIG. 5, but it will be appreciated that other mobile computing devices and/or other types of test can be implemented by the manual function test module 80.

The setup module 82 can facilitate setting up the manual function test, such as can include data 90 specifying that the housing of the nine-hole peg test has been positioned on the touch screen, which can be automatically detected by the touch screen or in response to user input. Additional data setup data 92 can be provided to specify that the pegs of the nine-hole peg test have also been positioned to their respective starting position, which can be detected automatically or in response to a user input responding to query. In an example, the mobile computing device executing the test module 80 can be a tablet computer (e.g., an iPad tablet computer available from Apple, Inc.). The housing of the test apparatus (housing 72 of FIG. 5) can be positioned on the touch screen such that the holes in the housing can correspond to GUI input points on the touch screen. The pegs can be positioned in a row or in the discard tray depending on the test process. The pegs can be of a diameter smaller than the diameter of the holes and a length greater than the distance between the touch screen and the holes in the housing.

The data collection module 84 can collect data related to the nine-hole peg test. The data collection module 84 can record a position of each peg (e.g., in the X and Y direction) on the screen 94. The data collection module can sample the touch screen (e.g., via a touch screen API) for the detecting position data 96 representing a location each of the pegs at a predefined sample rate (e.g., about 60 Hz or a higher or lower rate). At each sampling interval, the time associated with any insertion and/or removal event of a peg can be recorded and stored in memory as insertion or removal data 98.

A data processing module 86 can be configured to process input data for subsequent analysis. For example, the data processing module can include a filter 100 to remove noise and artifacts from the collected data. For example, the filter can operate to remove artifacts due to "peg bounce" from data collected from the touch screen. The data processing module 86 can also be configured to identify a phase shift 102 from insertion of the peg to removal of the peg.

The data processing module can also include a timing monitor 103 to tracking timing associated with data collected during execution of the test module 80. For instance, the timing monitor 103 can determine factors, such as the total time to complete one cycle of insertion and removal of all 9 pegs. The timing monitor 103 for example can associate a time stamp to all input data, including position data 94 from the touch screen and force information from a force transducer. Additionally, the timing monitor 103 can also operate in conjunction with the touch screen interface to indicate a time of insertion and removal of each peg relative to location and removal from the well or home row, and the difference in time to complete the well and home row tasks.

In another example, the data collection module 84 can include a force calculator 101 programmed to compute force during a series of tasks for measuring the patient's manual dexterity. The manual function test module 80 can execute instructions, for example, to display a series of GUI objects on a display with which the user is to interact by employing one or more gripping apparatus (e.g., the external user input device 32 mentioned with respect to FIG. 1). As one example, the user can be instructed to select an appropriate gripping device and move an end of the device into engagement with a GUI object displayed on the touch screen. Different shapes and sizes of device can be used or a single generic gripping device can be used. In addition to measuring gripping force during the test, the force calculator 101 can compute other movement and force related information (e.g., force variability) based on the output of a force transducer with which the user interacts and/or interaction with the touch screen. For example, detected data from the force transducer can be communicated to the computer (e.g., via a wired or wireless link) and the force calculator can convert the data in a force measurement. The manual function test module 80 can also record other test information, such as timing based on the timing monitor 103 and other information attributes based on how the user moves the gripping device and how the user interacts with the touch screen during each task.

The data analysis module 88 can analyze the data and create the output data (e.g., MDTD) that is aggregated as part of the test data (e.g., TD) for future scoring. The data analysis module 88 can analyze one or more time parameters 104. The time parameters 104 can include a total time to complete the test, an insertion time for a peg, and/or a removal time for a peg. The time can also be computed as a time differential between any two sequential events. Statistical data (e.g., mean and standard deviation) related to the time values can also be computed and stored in memory. The data analysis module 88 can also measure a learning or fatigue effect 106 with the inter peg insertion or removal time, such as based on an analysis of how timing changes during execution of a given session of the manual function test module 80.

Figure 7:
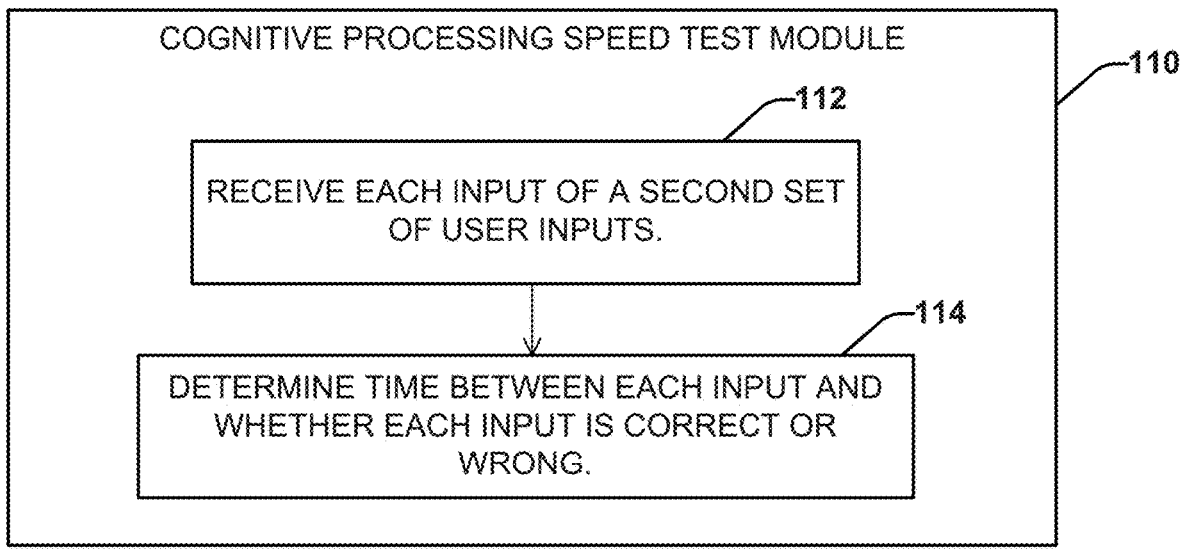
FIG. 7 depicts an example of a cognitive processing speed test module that can be used to evaluate a patient's cognitive processing speed.
Figure 8:
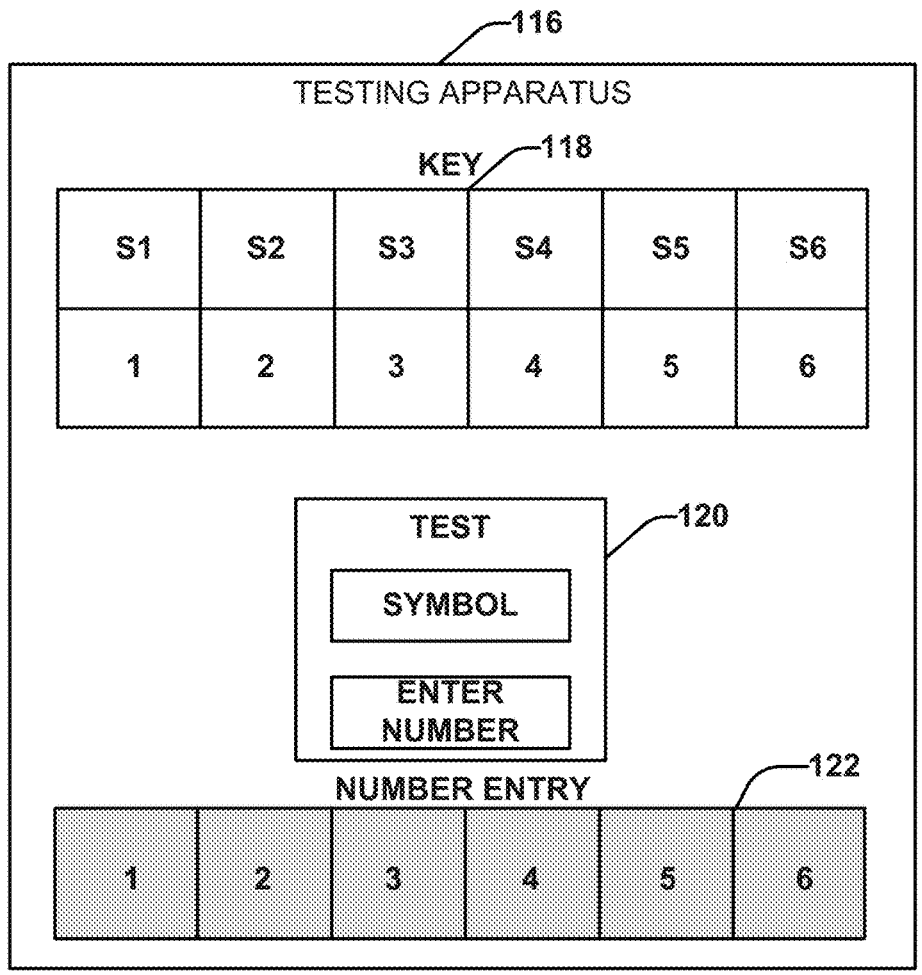
FIG. 8 depicts a schematic example of a cognitive processing speed test that can be used to evaluate a patient's cognitive processing speed.
Figure 9:
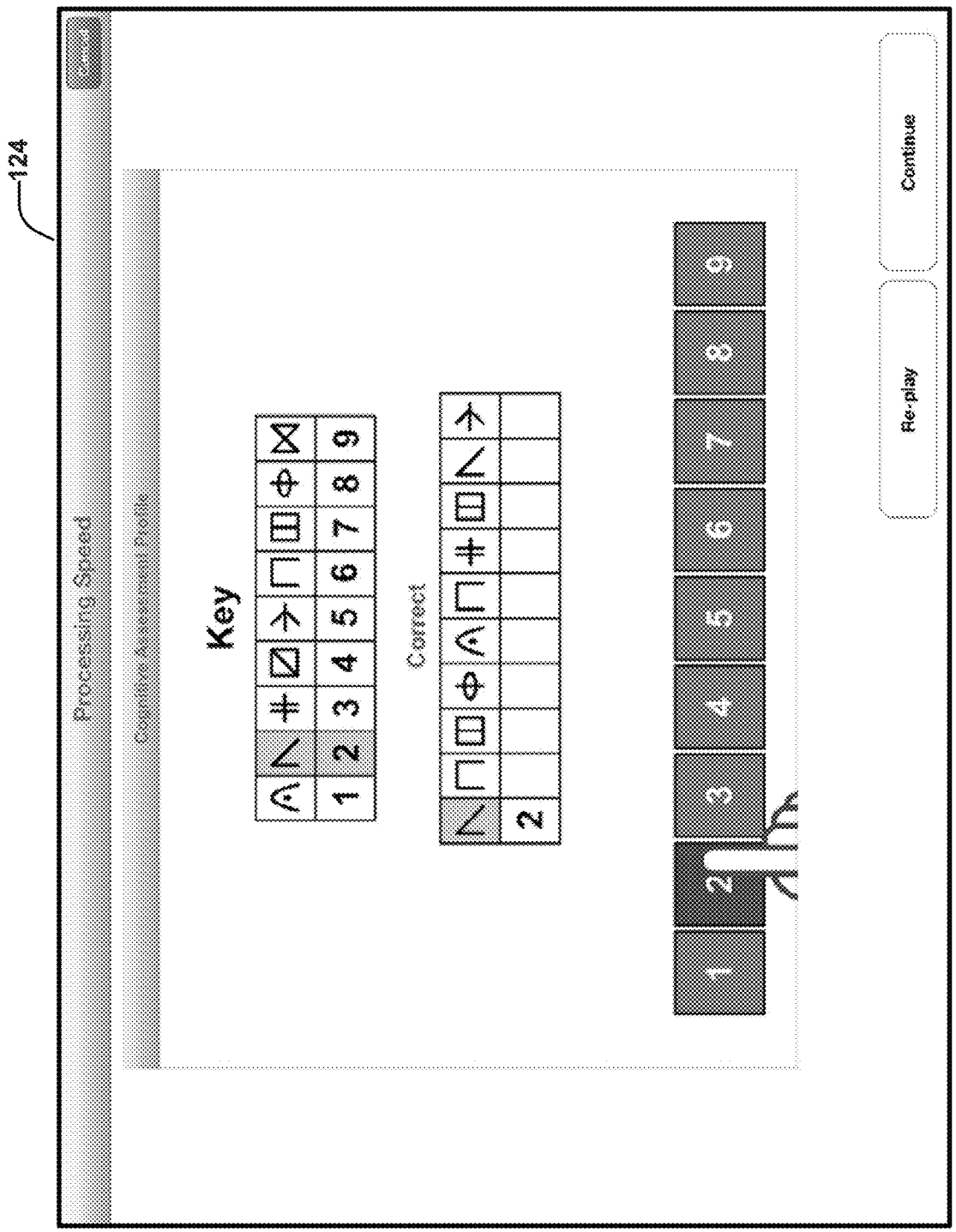
FIG. 9 depicts a screen shot of an example of cognitive processing speed tests that can be used to evaluate a patient's cognitive processing speed.
Figure 10:
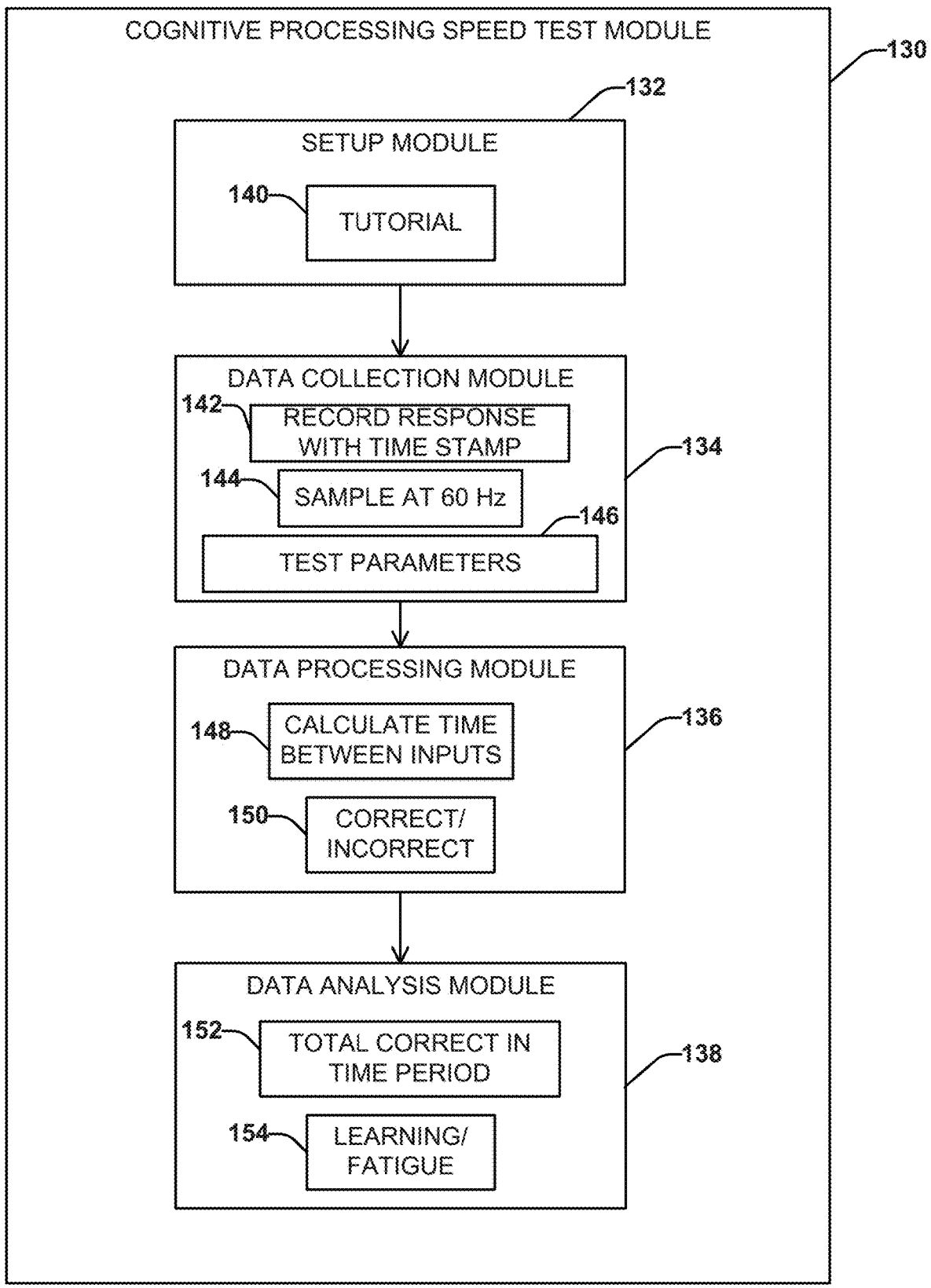
FIG. 10 depicts an example flow diagram demonstrating execution of a cognitive processing speed test module.

Examples of the cognitive processing speed test module that can be used to evaluate a patient's cognitive processing speed are shown in FIGS. 7-10. FIG. 7 depicts an example of a cognitive processing speed test module 110 that can be used to evaluate a patient's cognitive processing speed. FIGS. 8 and 9 depict a schematic examples screen shots for cognitive processing speed tests 116 and 124, respectively, that can be used to evaluate a patient's cognitive processing speed. FIG. 10 depicts an example flow diagram demonstrating the execution of the cognitive processing speed test module 130.

FIG. 7 depicts an example of a cognitive processing speed test module 110 that can be used to evaluate a patient's cognitive processing speed. The cognitive processing speed test module 110 can include a symbol generator, a key generator, a timing monitor and an analysis function. At element 112, each input of a set of user inputs can be received. The set of user inputs can be received from a user via a user interface, such as a touch screen of a mobile computing device (e.g., a tablet computer or a smart phone). At element 114, the time between each input can be determined. Also at element 114, whether the input is a correct or incorrect response to a prompt can be determined. The time and accuracy can be stored in memory. A score can be determined based on a number of correct responses in a time period for a speed test trail. The number of correct responses during the time period can be aggregated as part of the test data (TD). Additionally or alternatively, the score can be evaluated relative to pre-test data (from a control group and/or acquired during an un-timed pre-test).

As an example, overall test control can employ the cognitive speed processing test module 60 to implement a test (e.g., using the computing apparatus 12 of FIG. 1) to require that a user repeatedly associate a symbol (e.g., a digit 1-6 of FIG. 8) provided by the symbol generator with a random or pseudorandom key (e.g., S1-S6 of FIG. 9) generated by the key generator. Examples of the different symbols that can be associated with different numbers for the cognitive speed processing test module are shown in FIG. 9, depicts an example screen shot showing a GUI for implementing a processing speed test.

As shown in FIG. 8, the GUI can provide a key (e.g., randomly generated) and a sequence of characters that a user is to match during the testing 118. The randomly generated key can provide random number/signal pairings for each administration. The participant records responses by using the keyboard at the bottom of the screen 122. The middle section of the screen 120 is replaced with a new set a symbols when a response is recorded to the last symbol. The testing can record data indicative of both accuracy and speed for each phase of such testing. The processing speed test demonstrates comparable psychometric properties as the more traditionally used symbol digit modalities test.

The cognitive speed processing test module 110 can also be programmed to provide additional measures beyond simple measure of accuracy. The timing monitor can record the time to complete each task, the test a whole. The timing monitor can also be employed to supply a time base for interactions during the test. For example, if the user is dragging a graphical object (e.g., with a finger or stylus), timing can be utilized to compute acceleration and deceleration effects for such user interactive dragging events. Other cognitive functions tested by the cognitive speed processing test module 110 can include memory recall, attention and mental fatigue.

FIG. 10 depicts an example flow of the execution of the cognitive processing speed test module 130 that can evaluate a cognitive function of the given patient. The cognitive processing speed test module 130 can include a plurality of sub-modules, each of which can include one or more respective functions. As shown in FIG. 10, the sub-modules can include a setup module 132, a data collection module 134, a data processing module 136 and a data analysis module 138. FIG. 10 is described with respect to a tablet computer and in the context of the corresponding symbol digit modalities test shown in FIGS. 8 and 9, but it will be appreciated that other mobile computing devices and/or other types of tests can be implemented by the cognitive processing speed test module 130.

The setup module 132 can present an instructional tutorial 140 on the mobile computing device to establish test competency. The data collection module 134 can collect data related to the nine-hole peg test, The data collection module 134 can record each response with a time stamp 142, sampling for responsive inputs at a suitable sample rate (e.g., about 60 Hz or a higher or lower rate) 144. The responsive inputs can also be recorded with respect to test parameters 146 (e.g., key and symbol layout). The data processing module 136 can include a time calculator 148 to calculate the time between the individual input responses. The data processing module 136 can also include a function 150 to determine whether each individual input response is correct or incorrect. The data analysis module 138 thus can analyze the data and store corresponding output data (e.g., CPSTD) that is aggregated as part of the test data (e.g., TD) for subsequent overall test scoring. The data analysis module 138 can determine the total score correct in the time period 152. The data analysis module 138 can also be programmed to identify any inter-trial learning or fatigue effect (and correct for these effects).

Figure 11:
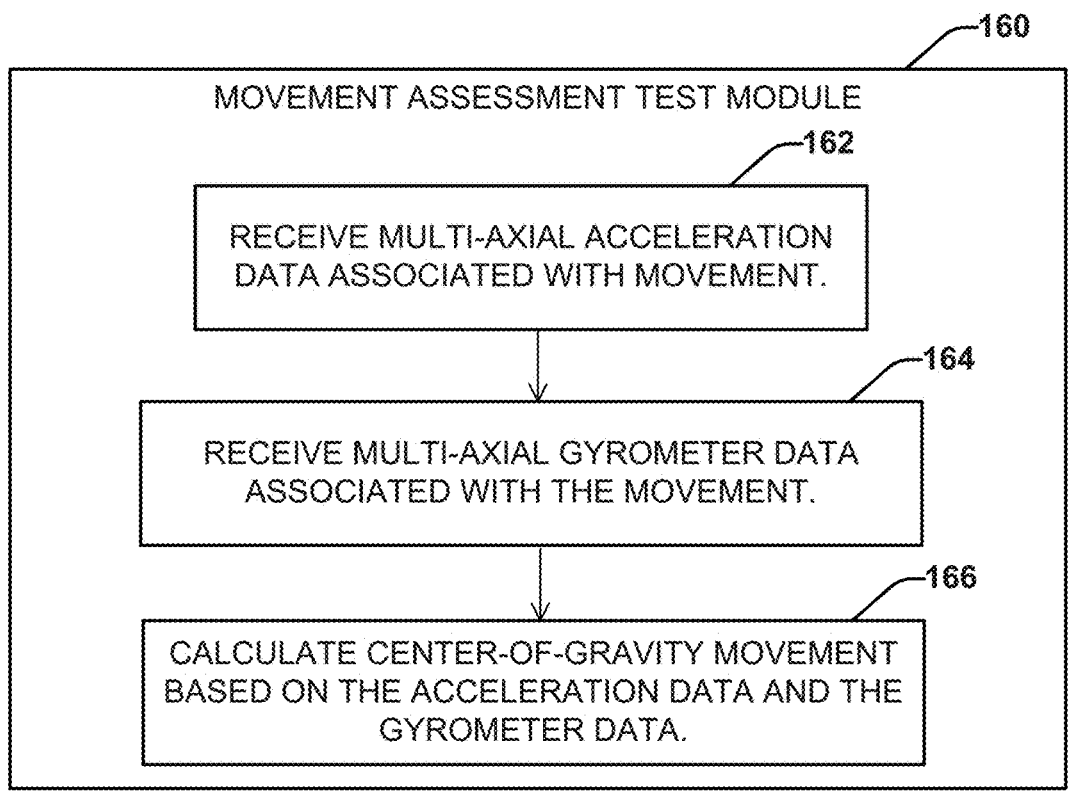
FIG. 11 depicts an example of a movement assessment test module that can be used to evaluate a patient's center-of-gravity movement.
Figure 12:
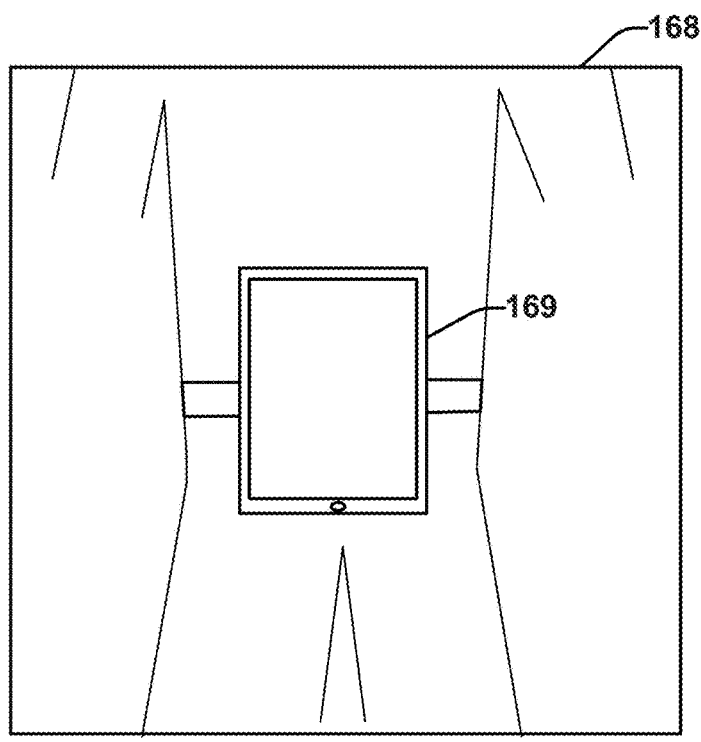
FIG. 12 depicts a schematic example of a mobile computing apparatus that can be attached to a patient for conducting one or more movement assessment tests to evaluate a patient's center-of-gravity movement.
Figure 13:
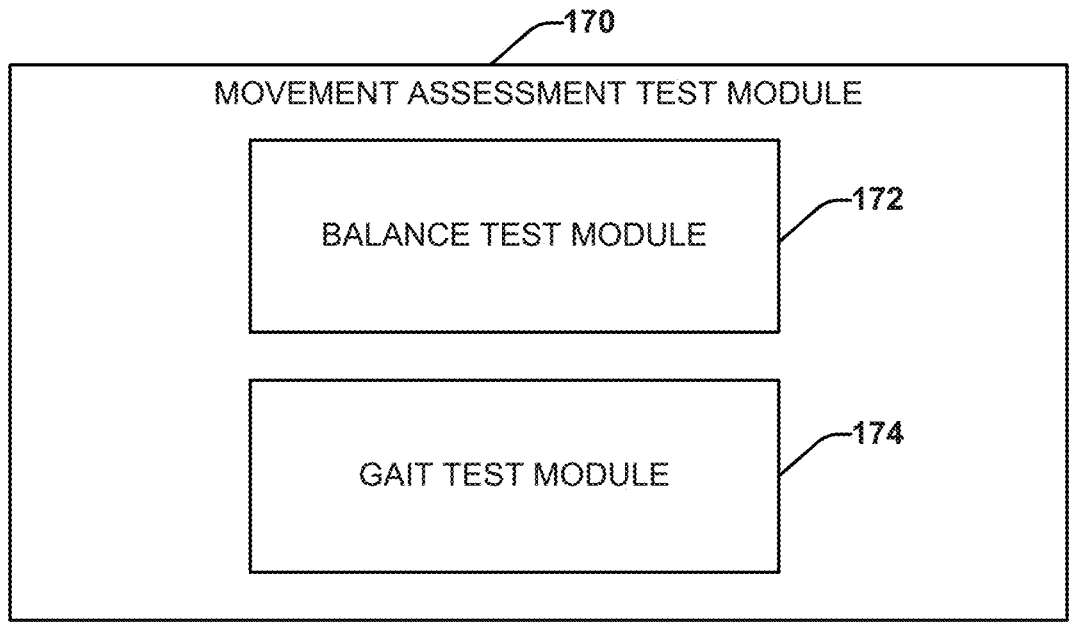
FIG. 13 depicts another example of a movement assessment test module that includes a balance test module and a gait test module.
Figure 14:
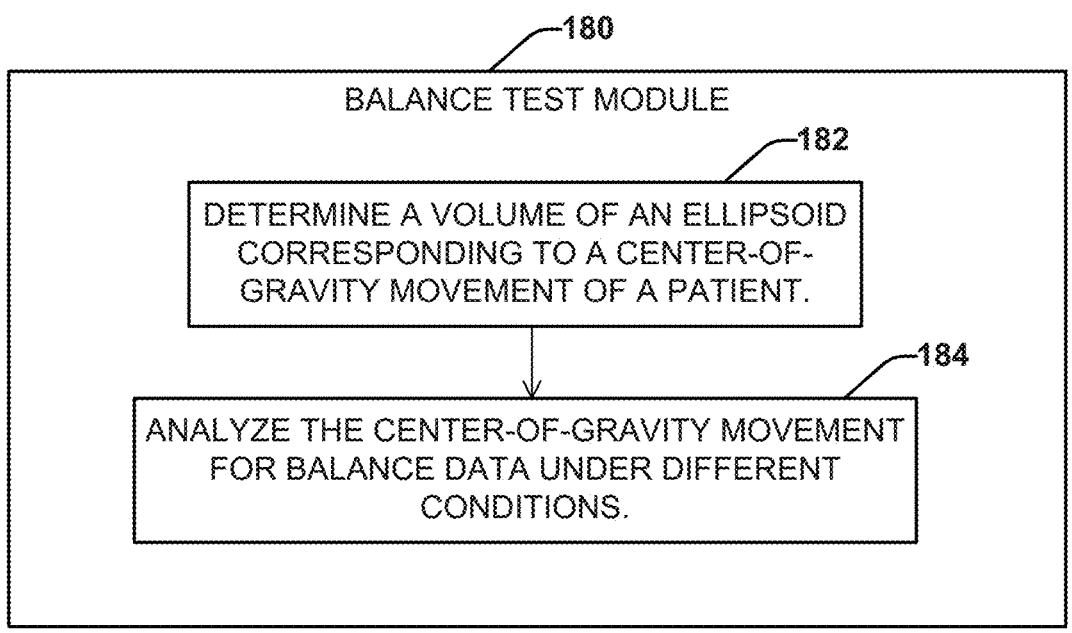
FIG. 14 depicts an example of a balance test module that can be utilized to evaluate a patient's balance based on a center-of-gravity movement.
Figure 15:
FIG. 15 depicts a screen shot of an example of part of a balance test that can be implemented on a mobile computer to evaluate a patient's balance.
Figure 16:
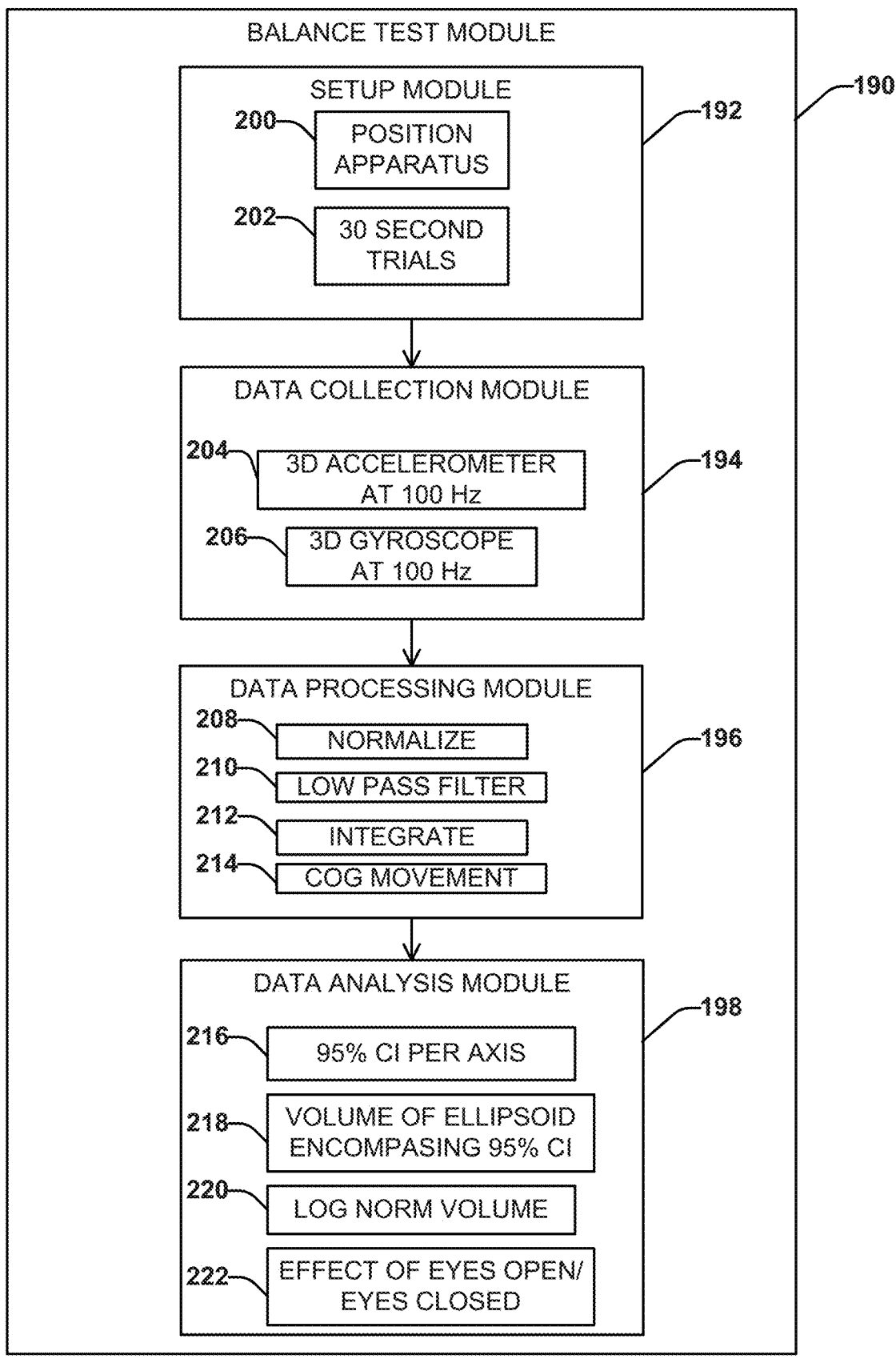
FIG. 16 depicts an example flow diagram demonstrating execution of a balance test module.
Figure 17:
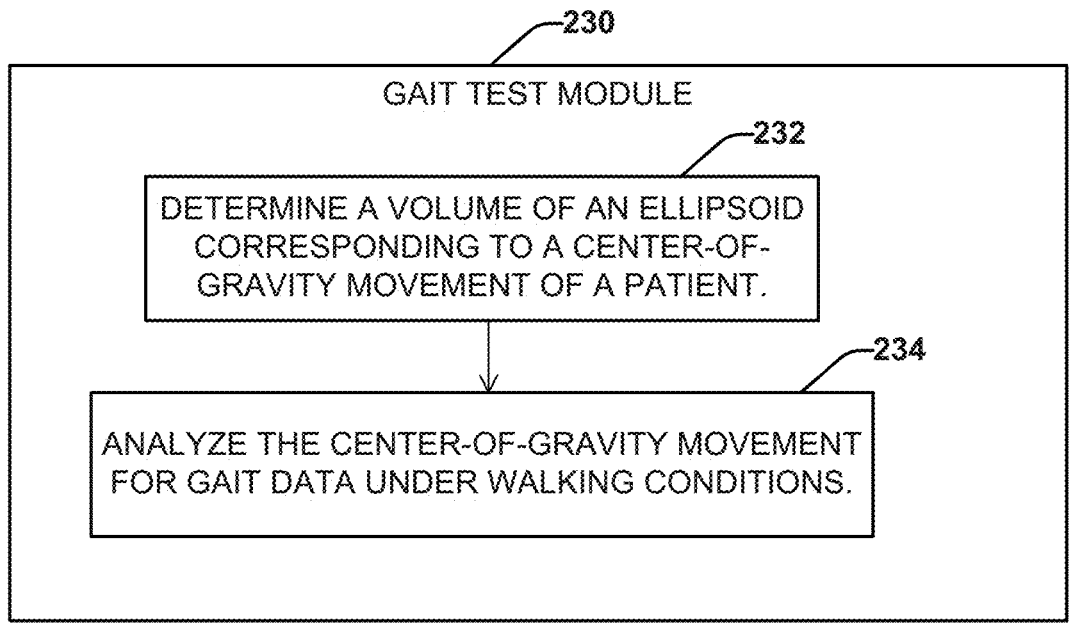
FIG. 17 depicts an example of a gait test module that can evaluate a patient's gait based on a center-of-gravity movement.
Figure 18:
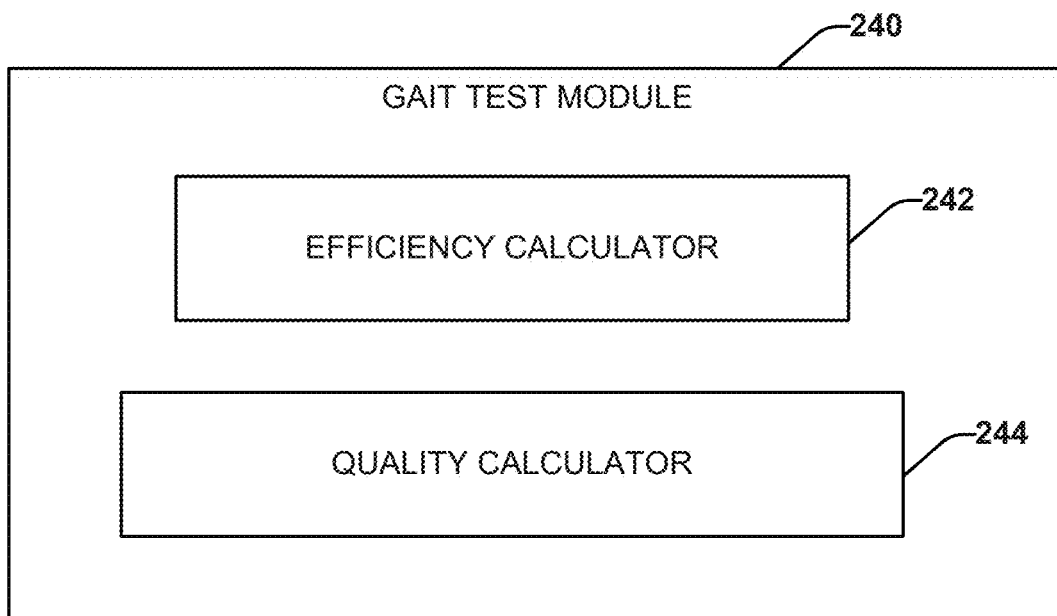
FIG. 18 depicts a schematic example of calculators that can be used by the gait test module to evaluate a patient walking a predetermined distance based on the patient's center-of-gravity movement.
Figure 19:
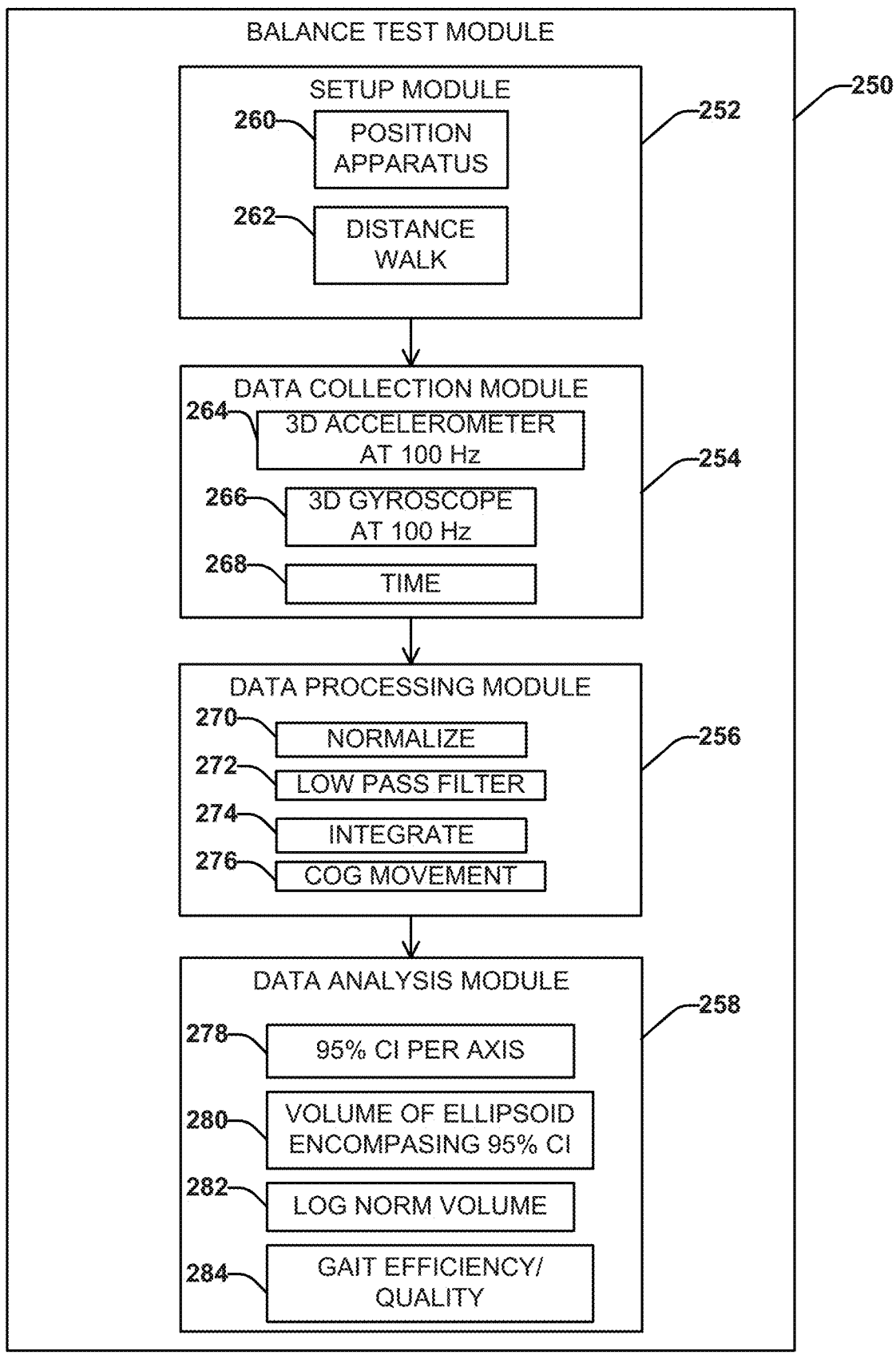
FIG. 19 depicts an example flow diagram demonstrating execution of the gait test module.

Examples of the movement assessment test module that can be used to evaluate a patient's center-of-gravity movement are shown in FIGS. 11-19. FIG. 11 depicts an example of a movement assessment test module 160 that can be used to evaluate a patient's center-of-gravity movement. FIG. 12 depicts a schematic example 168 of a computing device (e.g., mobile computer apparatus) 169 attached to a patient's body for conducting a movement assessment test. FIG. 13 depicts another example of a movement assessment test module 170 that includes a balance test module 172 and a gait test module 174. FIG. 14 depicts an example of a balance test module 180 that can evaluate a patient's balance based on a center-of-gravity movement. FIG. 15 depicts an example 186 of a balance test that can be used to evaluate a patient's balance. FIG. 16 depicts an example flow of the execution of the balance test module 190. FIG. 17 depicts an example of a gait test module 230 that can evaluate a patient's gait based on a center-of-gravity movement. FIG. 18 depicts a schematic example of calculators used by the gait test module 240 to evaluate a patient walking a predetermined distance based on the patient's center-of-gravity movement. FIG. 19 depicts an example flow of the execution of the gait test module 250.

FIG. 11 depicts a movement assessment test module 160 that can evaluate a center-of-gravity movement of the given patient in response to motion test data acquired during a physical activity (static or dynamic). The movement assessment test module 160 can receive accelerometer data (e.g., multi-axial accelerometer data associated with a movement 162) and gyrometer data (e.g., multi-axial gyrometer data associated with the movement 164). The accelerometer data and gyrometer data can be sampled from an accelerometer and gyroscope of the computing apparatus during a respective task. The tasks can include a balance task (e.g., provided by the balance test module 172 of the movement assessment test module 170 of FIG. 13) and/or a gait test (e.g., provided by the gait test module 174 of FIG. 13).

To complete the tasks, the patient can wear or hold the portable computing apparatus during a static test (e.g., balance test) or a dynamic test (e.g., gait test). For example, the movement assessment test module 160 of FIG. 11 can be executed by a computing device 169 while attached to the patient as demonstrated in FIG. 12. FIG. 12 demonstrates a mobile computing device (e.g., tablet computer or smart phone) 169 fixed on the patient's lower back at the sacral level. For instance, one or more straps or a belt 171 can be secured to the device and used to hold the computing device 169 on the patient's lower back during execution of the movement assessment test module 160 of FIG. 11. This testing configuration can be used for both static testing (e.g., balance test) and/or dynamic testing (e.g., gait test).

In FIG. 11, at element 166, the center-of-gravity movement can be calculated based on the acceleration data and the gyrometer data for the patient. The acceleration data and the gyrometer data can be acquired by one or more accelerometers and gyrometers in the computing device 169. An angular displacement can also be computed based on the gyrometer data, which can be part of the center-of-gravity movement computed by the test module 160 at 166. Movement assessment test module 160 can be programmed to translate the acceleration data and gyrometer data to the patient's center of gravity based on placement of the computing apparatus at a predetermined position during execution of the test module 160.

FIG. 14 depicts an example of a balance test module 180 that can be configured to evaluate a patient's balance based on a static center-of-gravity movement. The balance test module 180 can determine a volume of an ellipsoid in three-dimensional space corresponding to the center-of-gravity movement of the patient, demonstrated as function 182. A center-of-gravity movement during a static balance test corresponds to a lack of balance. The center-of-gravity movement is analyzed for balance data under different conditions, demonstrated as function 184. An example of the different conditions is shown in FIG. 15, which depicts an example screen shot 186 showing a GUI for a balance test. In this example, instructions are provided to the user on how to implement the test, such as can include plurality of tests for a predetermined duration. Data from sensors (e.g., one or more accelerometers, magnetometers and a gyroscope) can be collected during each test and a corresponding score can be computed based on such results.

FIG. 16 depicts an example flow of the execution of the balance test module 190 that can evaluate a balance function of the given patient. The balance test module 190 can include a plurality of sub-modules, each of which can include respective functions. As shown in FIG. 16, the sub-modules can include a setup module 192, a data collection module 194, a data processing module 196 and a data analysis module 198. FIG. 16 is described with respect to an tablet computer and the electronic analog of the balance test shown in FIG. 15, but it will be appreciated that other mobile computing devices and/or other types of tests can be implemented by the balance test module 190.

The setup module 192 can position 200 the testing apparatus on the patient's back and configure the time interval for the balance test (e.g., 30 second trials 202). The data collection module 194 can collect data from the accelerometer 204 and the gyroscope 206, each sampled at 100 Hz. The data processing module 196 can normalize 208 the data for initial apparatus orientation and placement, perform a low pass filter 210 operation on the data, integrate 212 the gyroscope data to resolve angular displacement and calculate time-series center-of-gravity (COG) movement 214 from accelerometer, gyroscope, and angular displacement data. The data analysis module 198 can analyze the data and create the output data that is aggregated as part of the test data (e.g., TD) for future scoring. The data analysis module 198 can determine a 95% confidence interval (CI) of time-series center-of-gravity movement per axis 216; a volume of an ellipsoid that encompasses the 95% CI; a log normalized volume 220; and a per-axis analysis for the effect of eyes open and eyes closed 222 conditions.

FIGS. 17 and 18 each depict examples of a gait test module 230, 240 that can be programmed to evaluate a dynamic condition (e.g., walking speed in a 25-foot walk test) for the patient. The evaluation can be based on the accelerometer data and gyroscope data, which can be used in the computation of a walking speed, a cadence, a stride length, and a variability in one or more of the other computed measures or other variations that might be determined from the acceleration and gyroscope data.

FIG. 17 depicts a gait test module 230 that can determine a volume of an ellipsoid corresponding to a center-of-gravity movement of the patient 232 and analyze the center-of-gravity movement for gait data under walking conditions 234. The analysis can be completed using the components of FIG. 18, an efficiency calculator 242 and a quality calculator 244. The efficiency calculator 242 can compute a measure of gate efficiency for each axis based on the center-of-gravity movement determined along each axis during a gait trial where the patient is walking a predetermined distance. The quality calculator 244 can compute a measurement of gate quality for each axis based on the center-of-gravity movement determined along each axis during the gait trial and based on the time for the patient to walk the predetermined distance.

FIG. 19 depicts an example flow of the execution of the gait test module 250 that can evaluate a dynamic motion task of the patient. The gait test module 250 can include a plurality of sub-modules. As shown in FIG. 19, the sub-modules can include a setup module 252, a data collection module 254, a data processing module 256 and a data analysis module 258. FIG. 19 is described with respect to an tablet computer, but it will be appreciated that other mobile computing devices and/or other types of tests can be implemented by the gait test module 250.

The setup module 252 can ensure that the apparatus is positioned on the patient's lower back 260, establish parameters for a 25-foot walking trial 262, and set a duration dependent on time to complete the 25-foot walk. The data collection module 254 can collect accelerometer data 264 (e.g., three dimensional accelerometer data from the apparatus) and gyroscope data 266 (e.g., three dimensional gyroscope data from the apparatus) both sampled at 100 Hz. The data collection module 254 can also determine a time for the patient to complete the 25-foot walk 268. The data processing module 256 can normalize 270 the data for initial position (orientation and placement) of the apparatus, low pass filter the data 272, integrate 274 the gyroscope data to resolve angular displacement, and calculate the time-series center-of-gravity movement 276 from accelerometer, gyroscope, and angular displacement data. As an example, the data analysis module 258 can determine a 95% confidence interval (CI) of the time-series center-of-gravity movement per axis 278, determine a volume of ellipsoid that encompasses the 95% CI 280, log normalize the volume 282, and perform a per axis analysis for measure of gait efficiency and quality 284.

Figure 20:
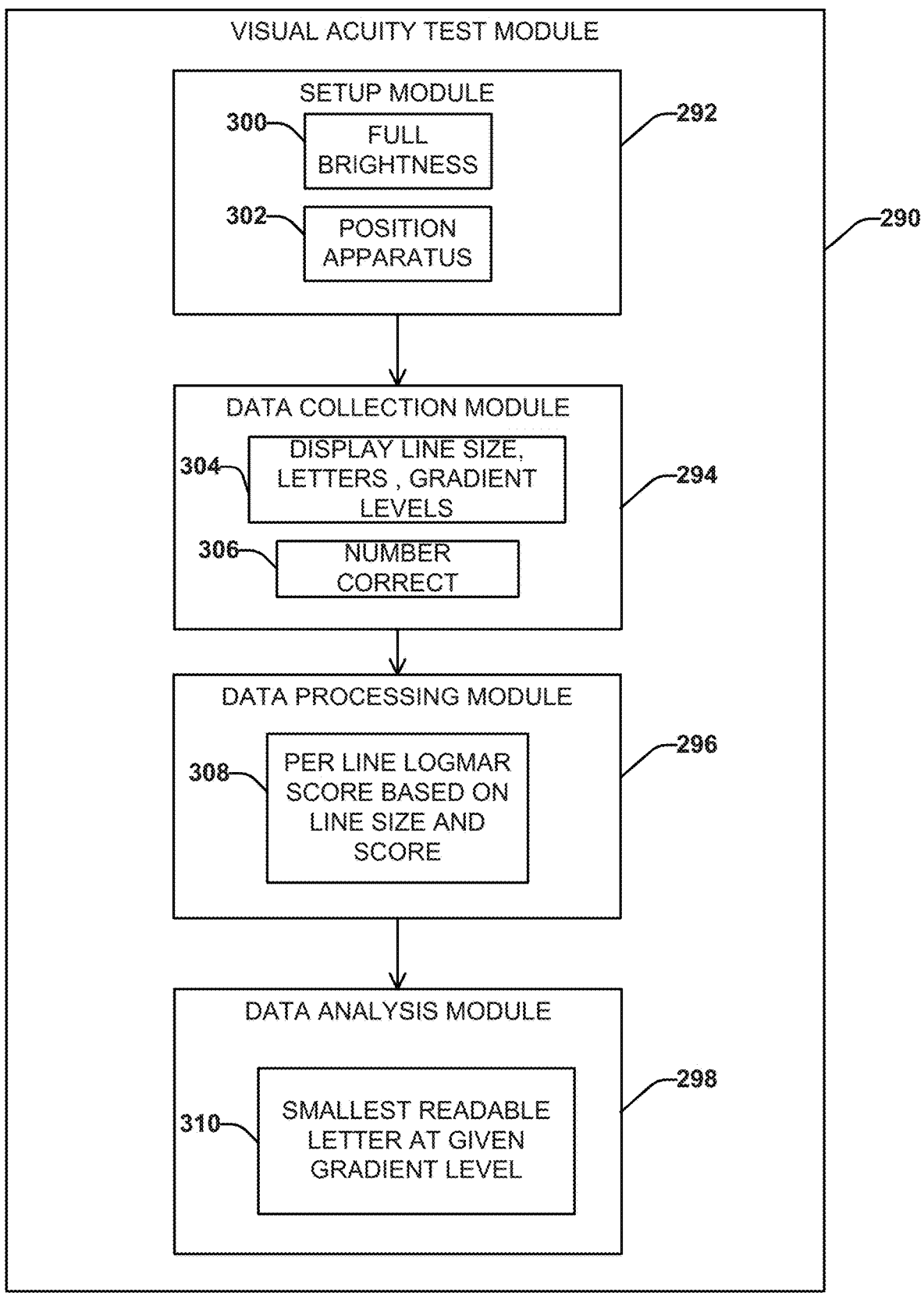
FIG. 20 depicts an example flow diagram demonstrating execution of a visual acuity test module.
Figure 21:
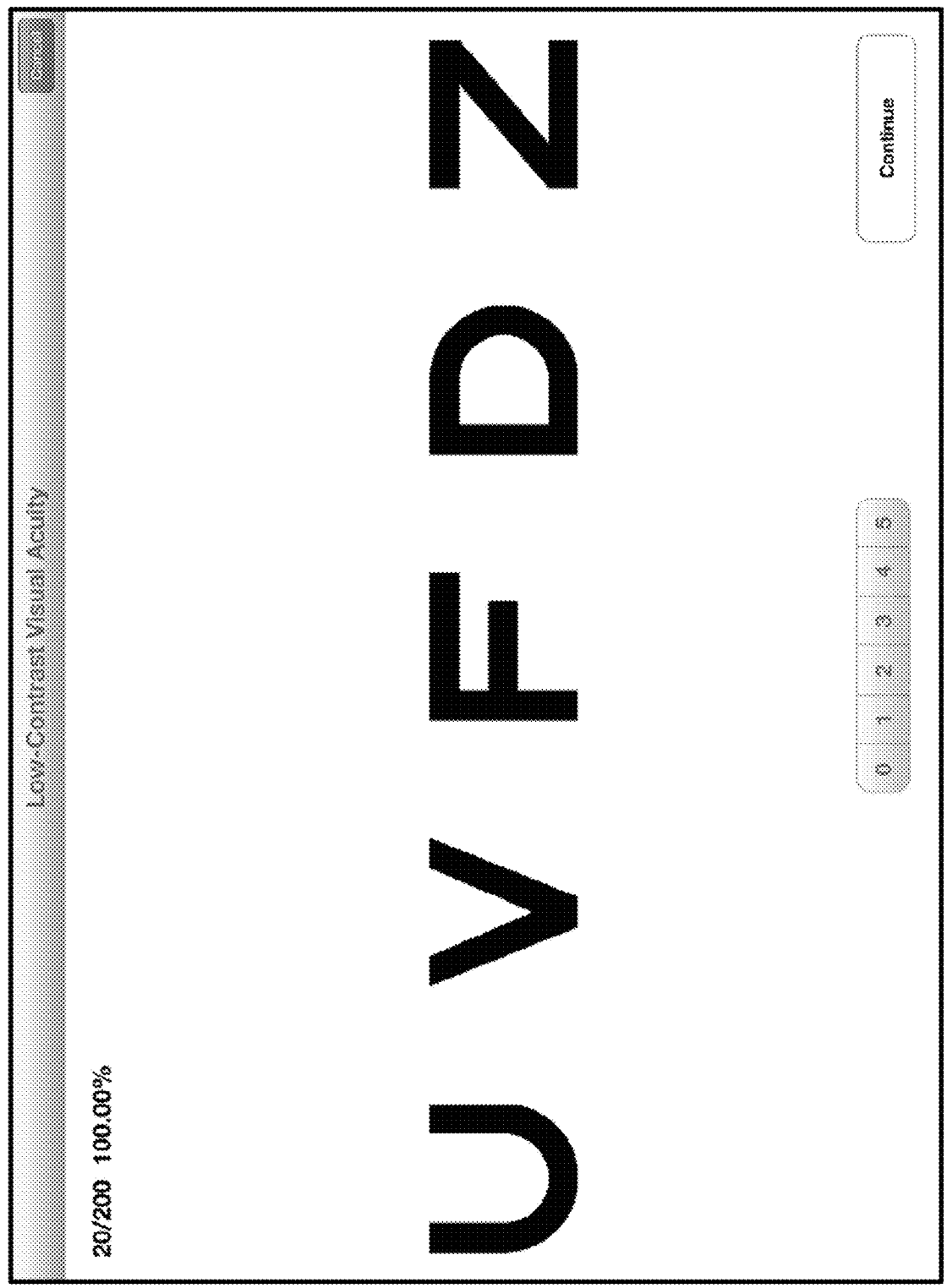
FIGS. 21-23 depict screen shots of examples of part of a visual acuity test that can be used to evaluate a patient's visual acuity.
Figure 22:
Figure 23:
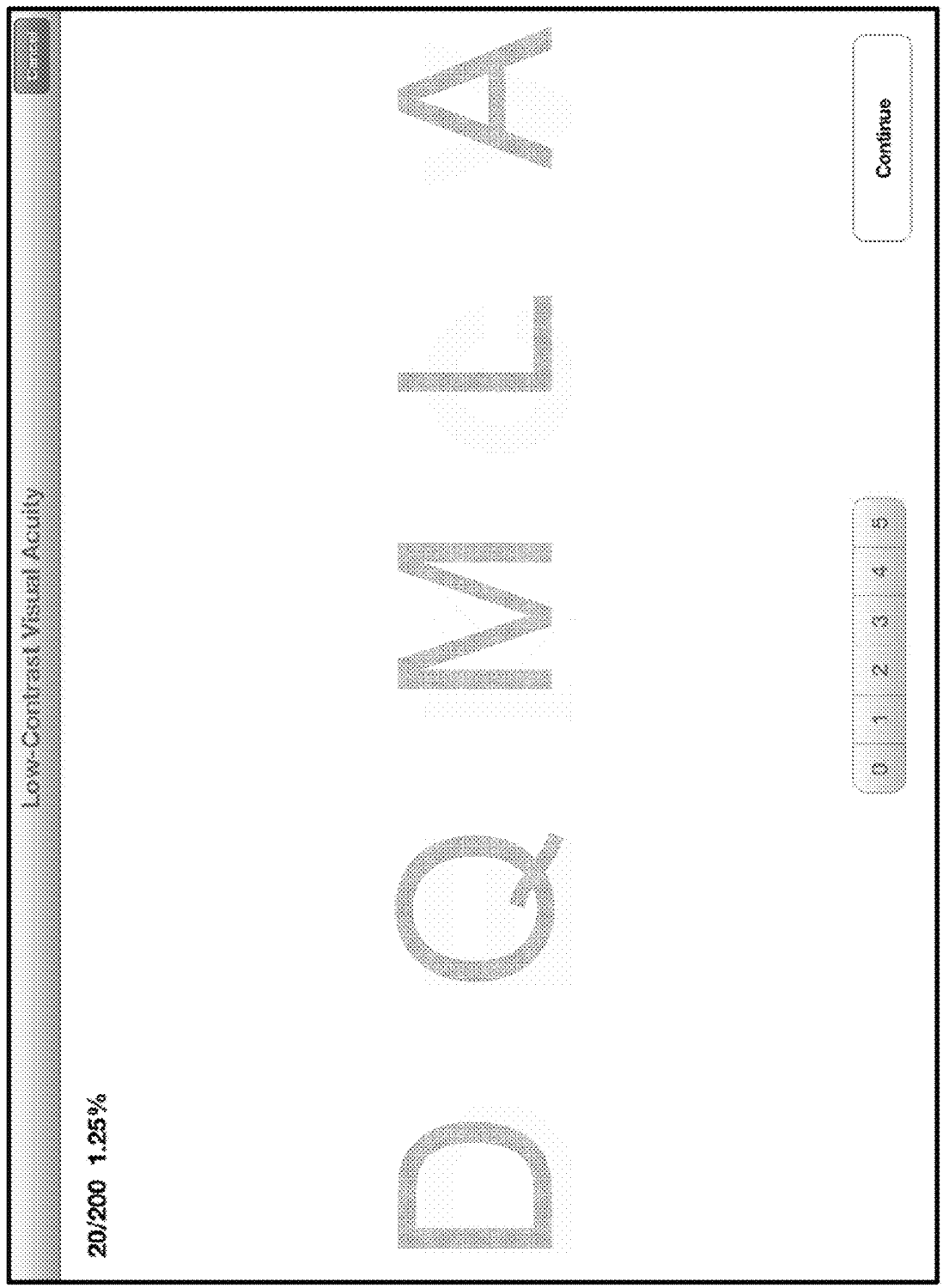

An example of an additional function test module (e.g., module 47 in FIG. 2 or module 57 in FIG. 3) is a visual acuity test module. The visual acuity test module can be programmed to evaluate visual function of the patient in response to user inputs, which can be stored in memory as the UI device data. The visual acuity test module can include a contrast control such as to provide tests for both static and dynamic visual acuity. For example a first part of test can establish baseline static acuity data for the patient. Following the static visual acuity test, the contrast control can vary the contrast in a dynamic manner for a plurality of tests. The data between static and dynamic visual acuity can be analyzed to ascertain an indication of patient visual acuity. The data can include an accuracy level for the test as well as a time to complete each phase of the test. Examples of the visual acuity test module that can be used to evaluate a patient's center-of-gravity movement are shown in FIGS. 20-23. FIG. 20 depicts an example flow of the execution of the visual acuity test module 290. FIGS. 21-23 depict schematic examples of a visual acuity test that can be used to evaluate a patient's visual acuity.

FIG. 20 depicts an example flow that can be executed by the visual acuity test module 290. The visual acuity test module 290 can include a plurality of sub-modules, each of which can include one or more respective functions. As shown in FIG. 20, the sub-modules can include a setup module 292, a data collection module 294, a data processing module 296 and a data analysis module 298. FIG. 20 is described with respect to an tablet computer, but it will be appreciated that other mobile computing devices and/or other types of tests can be implemented by the visual acuity test module 290.

The setup module 292 can set the screen to full brightness 300 and position the apparatus 302 (e.g., 5 feet from the patient at eye level). The data collection module 294 can collect data regarding the line size, letters displayed, and gradient levels 304, as well as the number of correct responses 306 recorded per line (e.g., of a possible 5). The data processing module 296 can determine a per line log MAR score 308 that is calculated based on the line size and the score. The data analysis module 298 can determine the smallest readable letter at a given gradient level 310. The smallest readable letter can be aggregated as part of the total data (TD).

FIGS. 21-23 demonstrate examples of GUIs corresponding to different visual acuity tests that can be implemented for assessing a patient's visual function. In the examples of FIGS. 21-23 different levels of visual contrast are provided, such as can correspond to 100% contrast, 2.5% contrast and 1.25% contrast. Other levels of contrast can be provided for testing a range of visual acuity. The testing can record data indicative of accuracy for the test as well as speed for such testing in response to user inputs indicating each respective letter via a corresponding user input (e.g., keypad or keyboard).

In view of the foregoing, it will be appreciated that the data collected via the approach disclosed herein provides facilitates automated assessment of a plurality of tests. For example, the approach provides a patient-centered neurological performance system, it can be used in non-medical setting (autonomously by the patient at home or other remote location) as well as medical settings typically not equipped to provide certain types of healthcare, such as at rural hospitals. The data collected for each given patient for a test sessions can be used for patient evaluation as well as for management of the patient's condition. Additionally, since the cost of the test system is inexpensive compared to many existing systems, the systems and methods disclosed herein facilitate clinical research projects, including clinical trials.

The testing can be implemented, for example, via a tablet computer, and can employ a graphical user interface on a portable computing device to implement one or more neurological and neuropsychological performance test method. For instance, the test method(s) can be utilized to help characterize a patient's multiple sclerosis or other neurological disorder (e.g., Parkinson's or essential tremor). As disclosed herein, the method can be self-administered by the patient himself/herself (as opposed to traditional clinician supervised testing which needs to be done by a trained technician). Thus the approach disclosed herein facilitates distance-based monitoring such as through telemedicine. Additionally, since the testing can be self-administered, it enables a care provider (e.g. a physician) to monitor the patient's condition over time to determine the course of disease and the effect of intervention for each of a plurality of patients.

The care provider can access a database to retrieve test results for a plurality of different patients that conducted the test at different remote locations, via a tablet computer where a test was implemented or a remote computer (e.g., smart phone, desktop PC or the like). As a further example, the test results can be communicated to one or more providers. This can be done by simply reviewing the results on the computing device or the results can be sent to the provider(s) via a network connection, as disclosed herein.

The test results for one or more subjects, for example, can be stored in a database in a server for further analysis and comparison. For instance, test data can be aggregated for a plurality of patients, such as for clinical research (e.g., in MS), including clinical trials and other forms of clinical research. Such test results for multiple tasks completed over a different time intervals (e.g., over a period of a day or a given week) can be evaluated to set one or stimulation parameters.

As will be appreciated by those skilled in the art, portions of the devices, systems and methods disclosed herein data processing system or computer program product. Accordingly, such features may take the form of an entirely hardware embodiment, an entirely software embodiment, or an embodiment combining software and hardware. Furthermore, portions of the invention may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain examples of the invention are described herein with reference to flowchart illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

What have been described above are examples. It is, of course, not possible to describe every conceivable combination of components or methodologies, but one of ordinary skill in the art will recognize that many further combinations and permutations are possible. Accordingly, the invention is intended to embrace all such alterations, modifications, and variations that fall within the scope of this application, including the appended claims. As used herein, the term "includes" means includes but not limited to, the term "including" means including but not limited to. The term "based on" means based at least in part on. Additionally, where the disclosure or claims recite "a," "an," "a first," or "another" element, or the equivalent thereof, it should be interpreted to include one or more than one such element, neither requiring nor excluding two or more such elements.

What is claimed is:

1. A system, comprising:
a housing configured to be removeably placed above a touchscreen interface comprising a plurality of apertures for conducting an electronic analog of a peg test; and
a mobile computing device comprising:
the touchscreen interface;
memory to store computer executable instructions corresponding to an application and data; and
a processor configured to access the memory and execute the computer executable instructions corresponding to the application, which comprise:
a manual function test module to evaluate a manual dexterity of a patient based on a first set of user inputs related to the electronic analog of the peg test, wherein the electronic analog of the peg test comprises a user interface to recognize contact with a physical peg extending within a respective aperture of the housing, and wherein the first set of user inputs comprise data provided by the touchscreen interface in response to contact or non-contact of a plurality of the physical pegs relative to predefined positions on the touchscreen interface, and to store corresponding manual dexterity test data in the memory indicative of a measure of the patient's manual dexterity;
a cognitive function test module programmed to evaluate a cognitive function of the patient based on a second set of user inputs to the touchscreen interface related to a cognitive processing speed test and to store corresponding cognitive function test data in the memory based on the second set of user inputs indicative of the patient's cognitive function;
a gait test module programmed to evaluate a walking speed of the patient over a distance and to store corresponding motion test data in the memory indicative of the patient's movement over the distance;
a visual acuity test module programmed to evaluate visual function of the patient in response to a third set of user inputs and to store corresponding visual acuity data in the memory indicative of the patient's visual acuity; and
a collection module to aggregate test data based on the manual dexterity test data, the cognitive function test data, visual acuity data and the motion test data and to provide an indication of neurological function for the patient based on the aggregate test data.

2. The system of claim 1, wherein the visual acuity test module further includes a contrast control to vary contrast of the touchscreen interface in a dynamic manner for a plurality of dynamic tests to provide dynamic visual acuity data for the patient.

3. The system of claim 2, wherein the contrast control of the visual acuity test module is further programmed to implement a static acuity test in which the contrast is fixed during the static acuity test and to establish baseline static acuity data for the patient, and
wherein the visual acuity test module is further programmed to analyze the baseline static acuity data for the patient and the dynamic visual acuity data for the patient to determine an indication of contrast sensitivity for the patient.

4. The system of claim 1, wherein the cognitive function test module comprises a graphical user interface that displays symbols and corresponding alphanumeric keys on the touchscreen interface and provides the cognitive function test data in response to user inputs received via the touchscreen interface to provide an indication of at least one of accuracy and speed for matching symbols and/or alphanumeric keys within a given time period.

5. The system of claim 1, wherein the cognitive function test module is configured to measure a time between responses entered via a user interface in response to the second set of user inputs, the time between responses and whether the response is correct or wrong being stored as part of the cognitive function test data.

6. The system of claim 5, wherein the cognitive function test module is further configured to determine a score based on a number of correct responses in a time period for a speed test trial and to evaluate the score relative to other stored test score data.

7. The system of claim 1, wherein the manual function test module is further configured to calculate a peg insertion time corresponding to a time interval from a first start time until contact of a given peg with the touchscreen interface and a peg removal time corresponding to another time interval from a second start time until breaking contact of the given peg with the touchscreen interface.

8. The system of claim 7, wherein the manual function test module is further configured to analyze the peg insertion time and the peg removal time for a plurality of peg insertion and peg removal events by the patient during a respective session of the manual function test module to provide an indication of at least one of learning or fatigue by the patient during the respective session.

9. The system of claim 1, wherein the collection module is further programmed to determine a composite score for the patient based on the manual dexterity test data, the cognitive function test data, visual acuity data and the motion test data and to compare the composite score for the patient to a stored test data to ascertain the indication of neurological function for the patient.

10. The system of claim 9, wherein the stored test data includes at least one of prior test data for the patient or test data that has been be aggregated for a plurality of patients.

11. The system of claim 1, wherein the gait test module is further configured to compute a volume of an ellipsoid in three dimensional space corresponding to a center-of-gravity movement for the patient acquired while the patient is walking the distance.

12. The system of claim 11, wherein the gait test module comprises:
an efficiency calculator configured to compute a measure of gate efficiency for each axis based on the center-of-gravity movement determined along a plurality of axes during a gait trial and based on a time interval for the patient to walk the distance; and
a quality calculator configured to compute a measure of gate quality for each axis based on the center-of-gravity movement determined along each axis during the gait trial and based on the time interval for the patient to walk the distance.

13. One or more non-transitory machine readable media that includes instructions executable by one or more processors, the instructions programmed to perform a method comprising:
receiving manual dexterity test inputs via a touchscreen interface during an electronic analog of a peg test, wherein the electronic analog of the peg test comprises a user interface to recognize contact with a physical peg positioned within a respective aperture of a housing while applied to the touchscreen interface, and wherein the manual dexterity test inputs comprise data provided by the touchscreen interface in response to contact or non-contact of a plurality of the physical pegs relative to predefined positions on the touchscreen interface, and to store manual dexterity test input data indicative of a measure of the patient's manual dexterity;

evaluating a manual dexterity of a patient based on the manual dexterity test input data to provide manual dexterity test data;

receiving a set of cognitive function test inputs through the touchscreen interface during a cognitive function test;

evaluating a cognitive function of the patient based on the cognitive function test inputs to provide cognitive function test data related to a cognitive processing speed of the patient;

receiving motion input data representing a walking time of the patient over a distance;

evaluating the motion input data to provide corresponding motion test data indicative of the patient's walking speed;

receiving a set of visual function test inputs via the touchscreen interface during a visual acuity test;

evaluating visual function of the patient based on the visual function test inputs to provide visual acuity test data indicative of the patient's visual acuity;

aggregating the manual dexterity test data, the cognitive function test data, the motion test data and the visual acuity test data to compute a score for the patient that provides an indication of neurological function for the patient.

14. The media of claim 13, wherein the instructions are further programmed to vary contrast of a display of the touchscreen interface during the visual acuity test in a dynamic manner over a plurality of dynamic visual acuity tests to provide dynamic visual acuity data for the patient.

15. The media of claim 14, wherein the instructions are further programmed to:
implement a static acuity test in which the contrast is fixed during the static acuity test and to establish baseline static acuity data for the patient, and
to analyze the baseline static acuity data for the patient and the dynamic visual acuity data for the patient to ascertain an indication of contrast sensitivity for the patient.

16. The media of claim 13, wherein the instructions further comprise a graphical user interface that displays symbols and corresponding alphanumeric keys on the touchscreen interface during the cognitive function test and provides the cognitive function test data in response to user inputs received via the touchscreen interface to provide an indication of at least one of accuracy and speed for matching symbols and/or alphanumeric keys within a given time period.

17. The media of claim 16, wherein the instructions are further programmed to:
measure a time between responses entered via a user interface in response to the user inputs received via the touchscreen interface during the cognitive function test, the time between responses and whether the response is correct or wrong being stored as part of the cognitive function test data; and
determine a score based on a number of correct responses in a time period for a speed test trial and to evaluate the score relative to other stored test score data.

18. The media of claim 13, wherein the instructions are further programmed to calculate a peg insertion time corresponding to a time interval from a first start time until contact of a given peg with the touchscreen interface and a peg removal time corresponding to another time interval from a second start time until breaking contact of the given peg with the touchscreen interface.

19. The media of claim 18, wherein the instructions are further programmed to analyze the peg insertion time and the peg removal time for a plurality of peg insertion and peg removal events by the patient during a respective session of the electronic analog of the peg test to provide an indication of at least one of learning or fatigue by the patient during the respective session.

20. The media of claim 13, wherein the instructions are further programmed to:
determine a composite score for the patient based on the manual dexterity test data, the cognitive function test data, visual acuity data and the motion test data; and
compare the composite score for the patient to a stored test data to ascertain the indication of neurological function for the patient, wherein the stored test data includes at least one of prior test data for the patient or test data that has been be aggregated for a plurality of patients.

* * * * *